(12) United States Patent
Azhdarinia et al.

(10) Patent No.: US 9,408,928 B2
(45) Date of Patent: Aug. 9, 2016

(54) COMPOSITIONS FOR TARGETED IMAGING AND THERAPY

(75) Inventors: Ali Azhdarinia, Houston, TX (US); Ebrahim S. Delpassand, Houston, TX (US); Izabela Tworowska, Houston, TX (US); Jennifer Sims-Mourtada, Pearland, TX (US)

(73) Assignee: Radiomedix, Inc., Houston, TX (US)

( * ) Notice: Subject to any disclaimer, the term of this patent is extended or adjusted under 35 U.S.C. 154(b) by 656 days.

(21) Appl. No.: 12/057,066

(22) Filed: Mar. 27, 2008

(65) Prior Publication Data

US 2009/0087377 A1 Apr. 2, 2009

Related U.S. Application Data

(60) Provisional application No. 60/908,332, filed on Mar. 27, 2007.

(51) Int. Cl.
*C07F 13/00* (2006.01)
*A61K 51/08* (2006.01)
*A61K 51/04* (2006.01)
*A61K 51/12* (2006.01)

(52) U.S. Cl.
CPC ........... *A61K 51/088* (2013.01); *A61K 51/0482* (2013.01); *A61K 51/0491* (2013.01); *A61K 51/0493* (2013.01); *A61K 51/0497* (2013.01); *A61K 51/08* (2013.01); *A61K 51/1244* (2013.01); *A61K 51/1248* (2013.01)

(58) Field of Classification Search
CPC ..... A61K 49/06; A61K 49/101; A61K 49/12; A61K 49/14; A61K 49/16; A61K 49/085; A61K 49/10; A61K 49/00; A61K 49/0036; A61K 49/0054; A61K 51/0485; A61K 51/00; A61K 51/04; A61K 51/041; A61K 51/044; A61K 51/0497; A61K 51/06; A61K 51/08; A61K 51/10; A61K 51/0474; A61K 51/0482; A61K 51/1248; A61K 51/0491; A61K 51/0493; A61K 51/244; C07D 257/02; C07D 257/00; C07D 487/22
USPC ........... 424/1.11, 1.41, 1.49, 1.53, 1.65, 1.69, 424/9.1, 9.2, 9.3, 9.4, 9.5, 9.6, 9.7, 9.8, 424/1.73, 9.36, 9.361, 9.362, 9.363, 9.364; 534/7, 10–16; 206/223, 569, 570; 514/1, 1.1, 788
See application file for complete search history.

(56) References Cited

U.S. PATENT DOCUMENTS

| | | | |
|---|---|---|---|
| 4,141,654 A | 2/1979 | Wardlaw et al. | |
| 4,988,496 A * | 1/1991 | Srinivasan et al. | 424/1.53 |
| 5,175,343 A * | 12/1992 | Fritzberg et al. | 560/145 |
| 5,242,679 A * | 9/1993 | Fritzberg et al. | 424/1.53 |
| 5,364,613 A * | 11/1994 | Sieving et al. | 424/9.3 |
| 5,605,672 A | 2/1997 | Bogdanov et al. | |
| 5,648,063 A | 7/1997 | Gries et al. | |
| 5,652,361 A * | 7/1997 | Simon et al. | 540/474 |
| 5,880,281 A | 3/1999 | Argese et al. | |
| 6,071,490 A | 6/2000 | Griffiths et al. | |
| 6,565,828 B2 * | 5/2003 | Liu | 424/1.53 |
| 6,613,305 B1 | 9/2003 | Collins et al. | |
| 6,673,333 B1 * | 1/2004 | Meade et al. | 424/9.35 |
| 6,692,724 B1 | 2/2004 | Yang et al. | |
| 6,737,247 B2 | 5/2004 | Bogdanov et al. | |
| 7,586,102 B2 | 9/2009 | Mourtada et al. | |
| 8,758,723 B2 * | 6/2014 | Yang et al. | 424/1.49 |
| 2002/0076379 A1 | 6/2002 | Platzek et al. | |
| 2006/0182687 A1 | 8/2006 | Yang et al. | |
| 2007/0048216 A1 | 3/2007 | Norenberg | |
| 2007/0297976 A1 | 12/2007 | Yang et al. | |
| 2014/0228551 A1 | 8/2014 | Tworowska et al. | |
| 2014/0271482 A1 | 9/2014 | Low et al. | |
| 2014/0275533 A1 | 9/2014 | Kularatne et al. | |

FOREIGN PATENT DOCUMENTS

| | | |
|---|---|---|
| CA | 2361115 A1 | 7/2000 |
| WO | 2006/121889 A2 | 11/2006 |
| WO | 2008-119036 A2 | 10/2008 |
| WO | 2009-108868 A2 | 9/2009 |

OTHER PUBLICATIONS

Moulin et al (Analytica Chimica Acta, 1999, vol. 378, Nos. 1-3, pp. 47-54).*
Smith, Journal of Inorganic Biochemistry, 2004, vol. 98, pp. 1874-1901.*
Froidevaux et al, Int. J. Cancer, 2002, vol. 98, pp. 930-937.*
Huskens et al, Inorganic Chemistry, 1997, vol. 36, No. 7, pp. 1495-1503.*
International Preliminary Report on Patentability and Written Opinion dated Nov. 26, 2009, from the International Bureau, in related International Application No. PCT/US2008/058476 (8 pages).
Al-Nahhas et al., "What can gallium-68 PET add to receptor and molecular imaging?", Eur J Nucl Med Mol Imaging., Dec. 2007, 1897-901, vol. 34(12).
Boswell et al., "Optimization of labeling and metabolite analysis of copper-64-labeled azamacrocyclic chelators by radio-LC-MS", Nucl Med Biol., Jan. 2005, 29-38, vol. 32(1).
Chappell et al., "Synthesis and evaluation of novel bifunctional chelating agents based on 1,4,7,10-tetraazacyclododecane-N,N',N'',N'''-tetraacetic acid for radiolabeling proteins", Nucl Med Biol., Aug. 2003, 581-95, vol. 30(6).
Engelhardt et al., "The Synthesis and Radiolabeling of 2-Nitroimidazole Derivatives of Cyclam and Their Preclinical E.pdf", J. Nucl. Med, 2002, 837-850, vol. 43.
Huskens et al., "Alkaline Earth Metal and Lanthanide(III) Complexes of Ligands Based upon 1,4,7,10-Tetraazacyclododecane-1,7-bis(acetic acid)", Inorg. Chem., 1997, 1495-1503, vol. 36 (7).

(Continued)

*Primary Examiner* — D L Jones
(74) *Attorney, Agent, or Firm* — JL Salazar Law Firm

(57) ABSTRACT

The present invention relates to the field of radiochemistry, nuclear imaging, radionuclide therapy and chemical synthesis. More particularly, it concerns a strategy for radiolabeling target ligands. It further concerns methods of using those radiolabeled ligands for imaging, radionuclide therapy and tissue-specific disease imaging.

16 Claims, 11 Drawing Sheets

(56) References Cited

OTHER PUBLICATIONS

Lecchi et al., "Current concepts on imaging in radiotherapy", Eur J Nucl Med Mol Imaging., Apr. 2008, 821-37, Vo. 35(4), Epub Oct. 31, 2007.
Maecke et al., "(68)Ga-labeled peptides in tumor imaging", J Nucl Med., Jan. 2005, 172S-8S, vol. 46(1).
Misra et al., "Biological and Clinical Aspects of Lanthanide Coordination Compounds", Bioinorg Chem Appl. 2004, 155-192, vol. 2(3-4).
Schmid et al., "Synthesis and evaluation of a radiometal-labeled macrocyclic chelator-derivatised thymidine analog", Nucl Med Biol. Apr. 2006, 359-66, vol. 33(3), Epub Mar. 9, 2006.
PCT International Search Report dated Jun. 30, 2008 (PCT/US08/58476).
PCT Written Opinion of the International Searching Authority dated Jun. 30, 2008 (PCT/US08/58476).
Lukes et al.; "Complexes of tetraazacycles bearing methylphosphinic/phosphonic acid pendant arms with copper (II), zinc (II) and lanthanides (III). A comparison with their acetic acid analogues"; Coordination Chemistry Reviews; Jun. 2001; vol. 216-217; pp. 287-312.
Smith; "Molecular imaging with copper-64"; Journal of Inorganic Biochemistry; Nov. 2004; vol. 98; No. 11; pp. 1874-1901.
Examiners Request (Office Action) dated May 19, 2011, issued by the Canadian Intellectual Property Office in related Canadian Patent Application No. 2,682,064 (5 pages).
Moulin, Christophe, et al., "Interaction studies between europium and a surfactant cage "TAC8" by time-resolved laser-induced fluorescence"; Analytica Chimica Acta 378 (1999); Elsevier Science B.V.; PII: S0003-2670(98)00644-8; pp. 47-54.
Examiners Requisition (Office Action) issued May 22, 2012, by the Canadian Intellectual Property Office in related Canadian Patent Application No. 2,682,064 (2 pages).
Extended European Search Report dated Nov. 15, 2012, issued by the European Patent Office in related European Patent Application No. EP-08732945.4 (18 pages.)
Gano, L., et al., "Radiolanthanide complexes with tetraazamacrocycles bearing methylphosphonate pendant arms as bone seeking agents"; The Quarterly Journal of Nuclear Medicine and Molecular Imaging, Original Articles, vol. 51, Mar. 2007, XP-002686621; pp. 6-15.
Szilagyi, Erika, et al., "Equilibria and formation kinetics of some cyclen derivative complexes of lanthanides"; Inorganica Chimica Acta 298 (2000); pp. 226-234.
Lukes, Ivan, et al., "Complexes of tetraazacycles bearing methylphosphinic/phosphonic acid pendant arms with copper(II), zinc(II) and lanthanides(III). A comparison with their acetic acid analogues"; Coordination chemistry Reviews 216-217 (2001); pp. 287-312.
Cable, Morgan L., et al., "Bacterial Spore Detection by [Tb3+(macrocycle)(dipicolinate)] Luminescence"; JACS Communications, Journal of the American Chemical Society, published on the Web Jan. 23, 2007; No. 129; pp. 1474-1475.
Yoo, Jeongsoo, et al., "Comparative in Vivo Behavior Studies of Cyclen-Based Copper-64 Complexes: Regioselective Synthesis, X-ray Structure, Radiochemistry, log P, and Biodistribution"; Journal of Medical Chemistry, vol. 47, 2004; pp. 6625-6637.
Dumont, Arnaud, et al., "Regioselective synthesis of 1,7-diprotected 1,4,7,10-tetraazacyclododecane and preparation of a dialcohol dicarboxylic macrocyclic ligand"; Tetrahedron Letters, vol. 35, No. 22, Elsevier Science Ltd. 1994; XP000605423; pp. 3707-3710.
Di Vaira, Massimo, et al., "Theoretical investigation on the geometries of DOTA and DOTA-like complexes and on the transition states of their conformational equilibria"; New Journal of Chemistry, vol. 26, 2002, DOI: 10.1039/b106168m; pp. 136-144.
Albert, Rainer, et al., "Direct Synthesis of [DOTA-DPhe1]-Octreotide and [DotaOTA-DPhe1,Tyr3]-Octreotide (SMT487): Two conjugates for Systemic Delivery of Radiotherapeutical Nuclides to Somatostatin Receptor Positive Tumors in Man"; Bioorganic & Medicinal Chemistry Letters 8 (1998); pp. 1207-1210.
Velikyan, Irina, Ph.D., et al., "Preparation and Evaluation of 68Ga-DOTA-hEGF for Visualization of EGFR Expression in Malignant Tumors"; Journal of Nuclear Medicine, No. 46, 2005; XP-002404435; pp. 1881-1888.
Di Vaira, Massimo, et al., "Synthesis and co-ordination chemistry of 1,7-bis(carboxymethyl)-4,10-bis(1-methylimidazol-2-ylmethyl)-1,4,7,10-tetraazacyclododecane"; J. Chem. Soc., Dalton Trans., published Jan. 1, 1998; pp. 1879-1884.
Trokowski, Robert, et al., "Selective Sensing of Zinc Ions with a PARACEST Contrast Agent"; Angew. Chem. Int. Ed., Magnetic Resonance Imaging, No. 44, 2005; DOI: 10.1002/anie200502173; pp. 6920-6923.
Patent Examination Report No. 1 (Office Action) issued Aug. 10, 2012, by the Australian Intellectual Property Office, in related Australian Patent Application No. 2008230771 (5 pages).
International Search Report and Written Opinion issued Jan. 31, 2013, by the International Searching Authority in International Patent Application No. PCT/US2012/043255 (8 pages).
Office Action mailed Mar. 29, 2013, in related Taiwan Patent Application No. 097112535, with English translation (12 pages).
Official Action issued Aug. 1, 2013, by the Mexico Patent Office in related Mexican Patent Application No. MX/a/2009/010412, with partial English translation (7 pages).
Official Action dated May 6, 2014, issued by the Mexican Patent Office in corresponding Mexican Patent Application No. MX/a/20091010412, with a partial English translation (14 pages).
Spanish and English version of Office Action for Mexican Patent Application No. MX/a/2009/010412 dated Jan. 28, 2015, 10 pages.
International Preliminary Report on Patentability in corresponding International Application No. PCT/US2012/043255 mailed Jan. 9, 2014 (5 pages).
English translation of Mexican Office Action dated Oct. 29, 2015 for counterpart Mexican Application No. Mx/a/2009/010412, 3 pages.
Schillaci, O. et al., "Fusion Imaging in Nuclear Medicine—Applications of Dual-Modality Systems in Oncology", Cancer Biother. Radiopharm., vol. 19, pp. 1-10 (2004)., 10 pages.
Gambhir, S. S. et al., "Imaging Transgene Expression With Radionuclide Imaging Technologies", Neoplasia, vol. 2, Nos. 1-2, Jan.-Apr. 2000, pp. 118-138., 21 pages.
Tjuvajev, Juri Gelovani et al., "Comparison of Radiolabeled Nucleoside Probes (FIAU, FHBG, and FHPG) for PET Imaging of HSV1-tk Gene Expression", The Journal of Nuclear Medicine, vol. 43, No. 8, Aug. 2002, pp. 1072-1083., 13 pages.
Reed, John C., "Apoptosis-targeted therapies for cancer", Cancer Cell, vol. 3, Jan. 2003, pp. 17-22., 6 pages.
Yaghoubi, Shahriar et al., "Human Pharmacokinetic and Dosimetry Studies of [18F]FHBG: A Reporter Probe for Imaging Herpes Simplex Virus Typw-1 Thymidine Kinase Reporter Gene Expression", The Journal of Nuclear Medicine, vol. 42, No. 8, Aug. 2001, pp. 1225-1234., 11 pages.
Ye, Yunpeng et al., "Polyvalent Carbocyanine Molecular Beacons for Molecular Recognitions", J. Am., Chem. Soc., vol. 126, 2004, pp. 7740-7741., 2 pages.
Mason, N. N Scott et al., "Positron Emission Tomography Radiochemistry", Neuroimag. Clin. N. Am., vol. 13 (2003), pp. 671-687., 17 pages.
Srivastava, Suresh C., "Is There Life After Technetium: What is the Potential for Developing New Broad-Based Radionuclides?", Seminars in Nuclear Medicine, vol. XXVI, No. 2 (Apr.) 1996, pp. 119-131., 13 pages.
Alauddin, Mian M., et al. "Synthesis of 9-[(3-[18 F]-fluoro-1-hydroxy-2-propoxy) methyl] guanine ([18 F]-FHPG): A potential imaging agent of viral infection and gene therapy using PET" Nuclear medicine and biology 23.6 (1996): 787-792., 6 pages.
Alauddin, Mian M., et al. "Evaluation of 9-[(3-18 F-fluoro-1-hydroxy-2-propoxy) methyl] guanine ([18 F]-FHPG) in vitro and in vivo as a probe for PET imaging of gene incorporation and expression in tumors." Nuclear medicine and biology 26.4 (1999): 371-376., 6 pages.
Alauddin, Mian M., and Peter S. Conti. "Synthesis and preliminary evaluation of 9-(4-[18 F]-fluoro-3-1ydroxymethylbutyl) guanine ([18

(56) References Cited

OTHER PUBLICATIONS

F] FHBG): a new potential imaging agent for viral infection and gene therapy using PET." Nuclear medicine and biology 25.3 (1998): 175-180., 6 pages.
Connors, Tom. "Anticancer drug development: the way forward." The Oncologist 1.3 (1996): 180-181., 2 pages.
Pan, Dongfeng, et al. "Rapid synthesis of a 5'-fluorinated oligodeoxynucleotide: a model antisense probe for use in maging with positron emission tomography (PET)." Bioorganic & medicinal chemistry letters 8.11 (1998): 1317-1320., 4 pages.
Gambhir, Sanjiv S., et al. "Imaging adenoviral-directed reporter gene expression in living animals with positron emission tomography." Proceedings of the National Academy of Sciences 96.5 (1999): 2333-2338., 6 pages.
Gambhir, Sanjiv S., et al. "A mutant herpes simplex virus type 1 thymidine kinase reporter gene shows improved sensitivity for imaging reporter gene expression with positron emission tomography." Proceedings of the National Academy of Sciences 97.6 (2000): 2785-2790., 6 pages.
Namavari, Mohammad, et al. "Synthesis of 8-[18 F] fluoroguanine derivatives: in vivo probes for imaging gene expression with positron emission tomography." Nuclear medicine and biology 27.2 (2000): 157-162., 6 pages.
Paulino, Arnold C., Wade L. Thorstad, and Timothy Fox. "Role of fusion in radiotherapy treatment planning." Seminars in nuclear medicine. vol. 33. No. 3. WB Saunders, 2003., 6 pages.
Remington's Pharmaceutical Sciences, 18th Ed., Mack Printing Company, 1990, pp. 1289-1329, 43 pages.
Proceedings of the fifty-fourth Annual Meeting, Microscopy Society of America; G. W. Bailey, J. M. Corbett, R. V. W. Dimlich, J. R. Michael and N. J., Zaluzec (Eds.). San Francisco Press, San Francisco, CA, pp. 898-899 (1996)., [online, retrieved from http://www.nanoprobes.com/applications/MSA96lip.html on Jan. 13, 2016], 3 pages.
Gatley, S. J., et al. "Radiopharmaceuticals for positron emission tomography. Development of new, innovative tracers for measuring the rates of physiologic and biochemical processes." Acta radiologica. Supplementum 374 (1989): 7-11., 6 pages.

\* cited by examiner

(a). Synthesis of DO2A-*bis*(*tert*-Bu) ester.
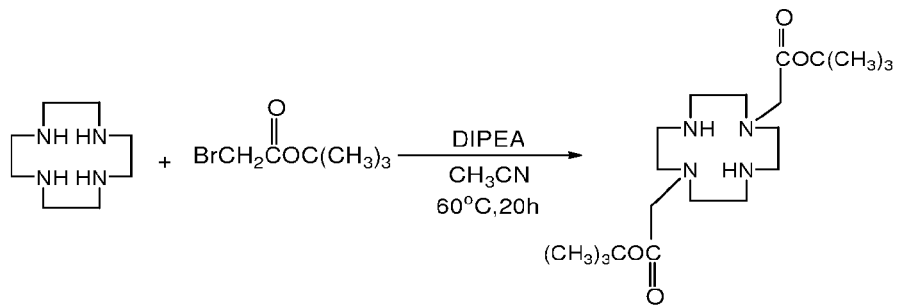
Z. Kovacs, A. D. Sherry, *J. Chem Soc., Chem, Commun.*, 1995, 185
(b). Schematic pathway of DO2S derivatives and DO2S derivative-1.
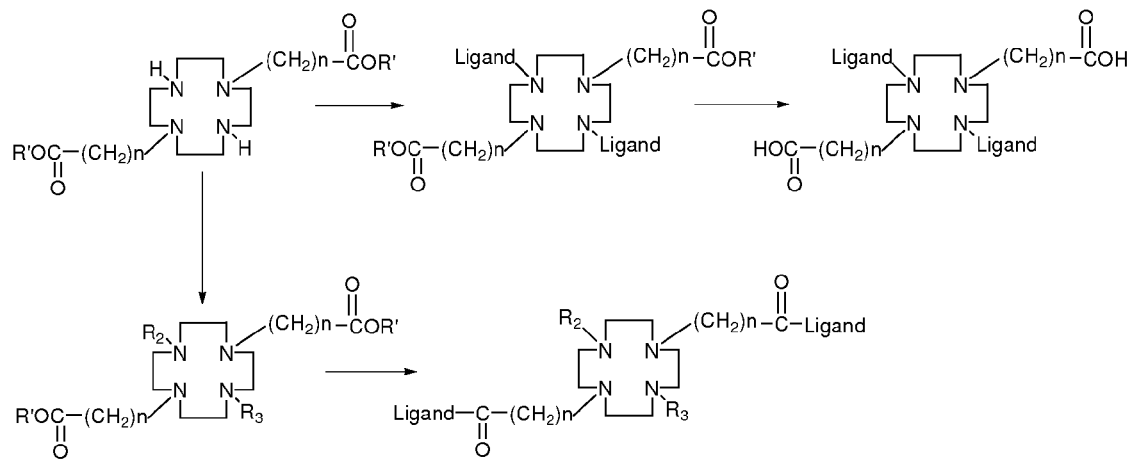
R'=protecting groups; $R_2, R_3 = (CH_2)_n NH_2$ or $(CH_2)_n COO^-$ or $CH_2(CH_2OCH_2)_n CH_2OH$; n=1-4
FIG. 1

Schematic structures of DO2S derivative-1 conjugates
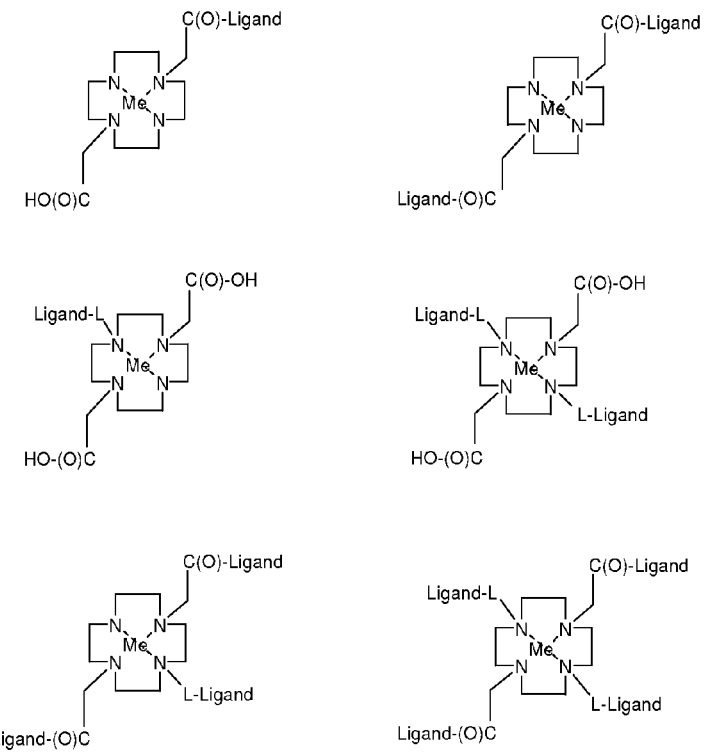
L= linker; -(CH$_2$)$_n$C(O)-, (CH$_2$)$_n$P(O)(O$^-$)-, (CH$_2$)$_n$-; n=1-4; Me= radioisotope
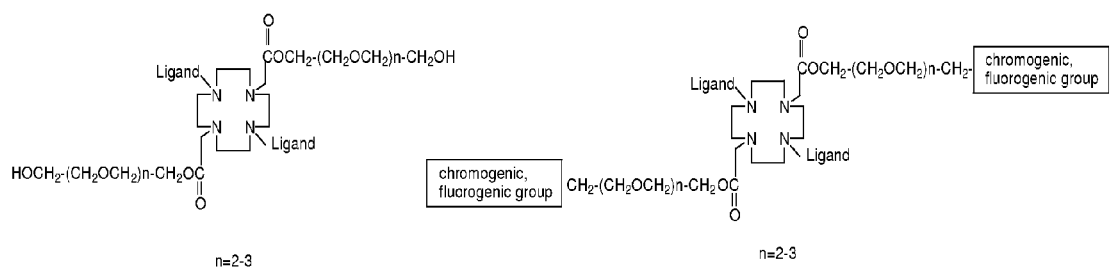
FIG. 1c

| | Ligand | Coupling reagents |
|---|---|---|
| 1. | Aminosugars (eg. glucosamine, galactosamine) | HBTU, HOBT, DIEA |
| 2. | Somatostatin analogs octreotide | |
| | a. directly attached | NHS, DCCI |
| | b. linker attached | HATU |
| 3. | EGF | NHS |
| 4. | Aliphatic and aromatic amines, amino acids, polyamines, peptides<br><br>Dual isotope labeling | HBTU, HOBT, DIEA<br><br>or *via* intermediate bromoacetyl bromide of aminoacids |
| 5. | Phosphate and phosphorothiate with lipophylic group (eg. cholesteryl, dipalmitolyl phosphatidyl ethanolamine)<br><br>Liposome derivatives | NHS |
| 6. | Carbon nanotubes, nanoparticles, gold nanoparticles (linker attached)<br><br>Dual labeling | DIEA |

FIG. 1d.

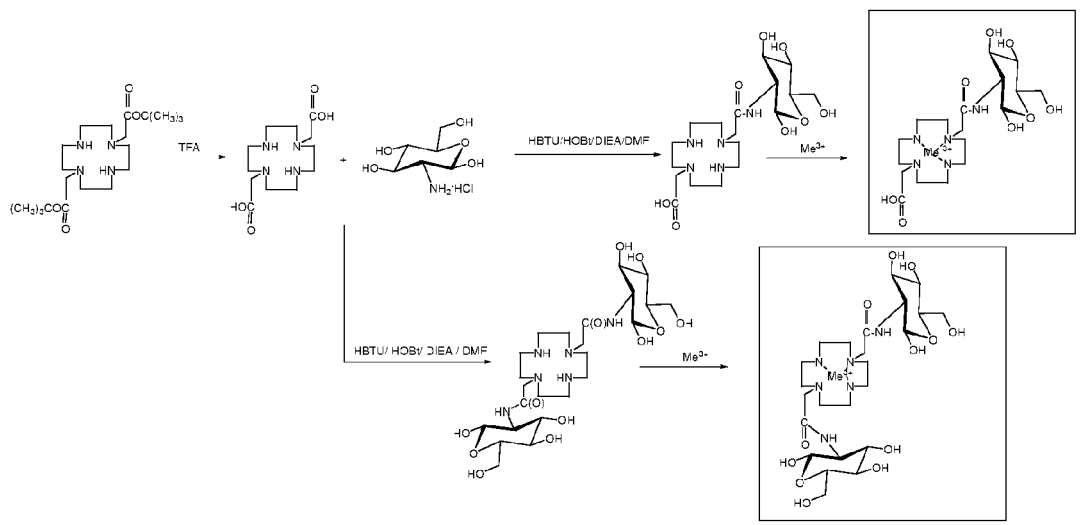

Deprotection of carboxyl groups of DO2A-*bis*(*tert*-Bu) ester or its derivatives proceed in the presence of TFA (trifluroacetic acid). The conjugation reaction of the DO2A-acid to the amino sugar (e.g. glucosamine hydrochloride, galactosamine hydrochloride) is performed by activation of carboxyl group of DO2A by HBTU (*O*-benzotriazole-*N,N,N',N'*-tetramethyluronium-hexafluorophosphate) and HOBT (1-hydroxybenzotriazole) in the presence of DIEA (*N, N*-diisopropylethylamine) in DMF. The selectivity of this reaction is controlled by the temperature and stoichiometry of reagents. Method is used to prepare of DO2S-dendrimers and their derivatives modified with polyamino sugar ligands.

Y. Ye, S. Bloch, S. Achilefu, *Journal of the American Chemical Society*, 2004, *126*, (25), 7740-7741.

FIG. 2

R₁= H or protecting group ; X = natural or non-natural amino acids with aliphatic or aromatic side chain;

X= natural and modified amino acids with aliphatic or aromatic side chain

| Linker: | PEG, n = any | ⌇⌇N(H)-CH₂CH₂-[O-]n-C(=O)-⌇⌇ |
|---|---|---|
| | Amino acids, peptides | eg. β-alanine, lysine, tris-glycine |
| | Asn-*N*-acetyl aminosugar<br>Asn-*N*-acetyl aminosugar | eg. D-glucosamine, D-galactosamine. |

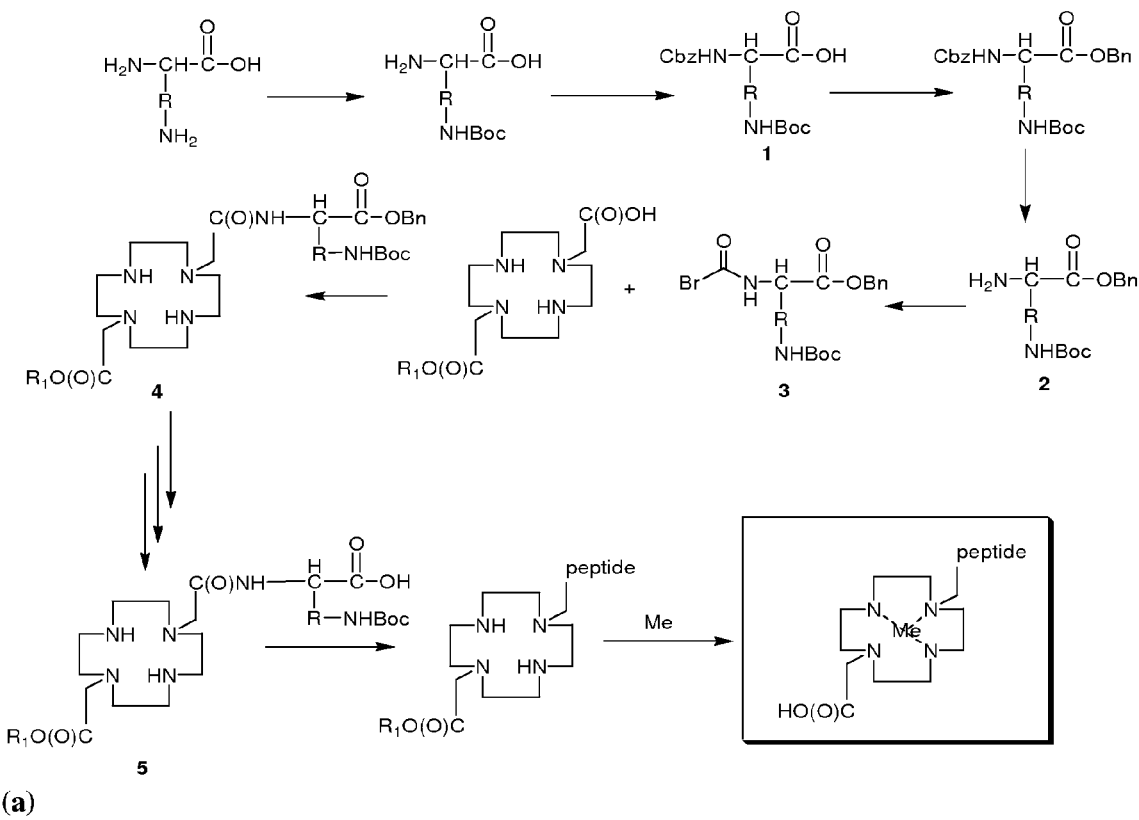
R= alkyl, amino acids; R₁ = protecting group;
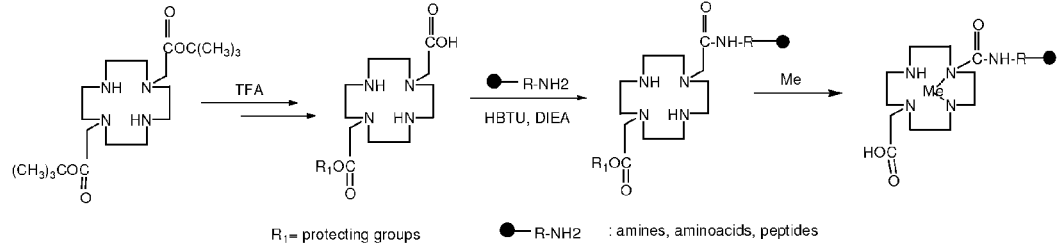
FIG. 5

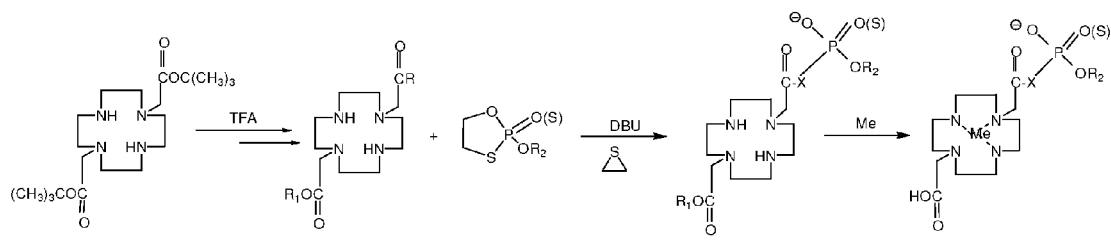
R= OH, NH₂; X=O, NH; R₁= protecting group;
R₂ = lipophylic groups eg.cholesteryl, dipalmitoyl phosphatidyl ethanolamine (DPPE)
Examples
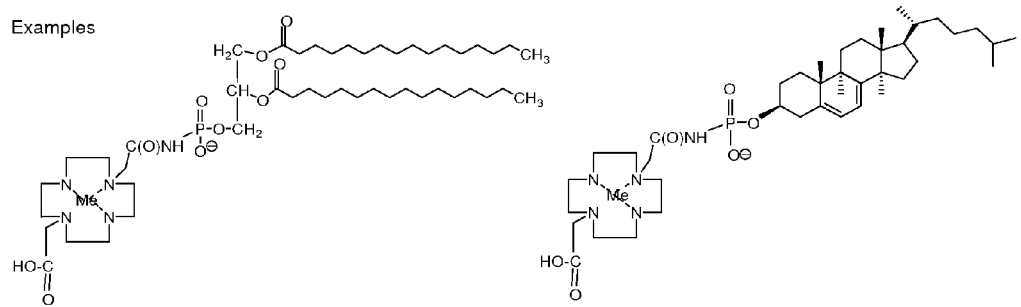
FIG. 6

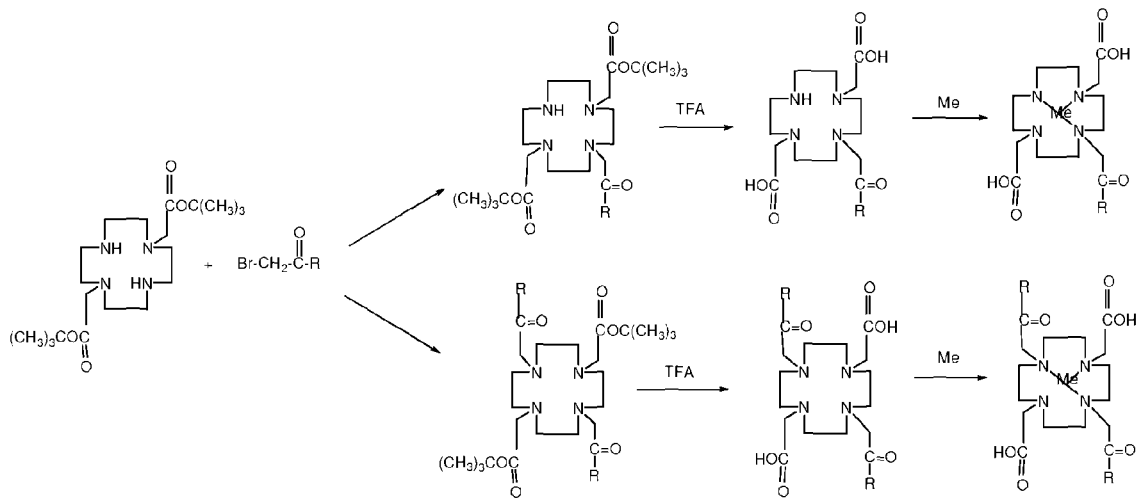
| R = | | |
|---|---|---|
| | PEG | |
| | Amino acids, peptides, aliphatic and aromatic amines | eg. beta-alanine, lysine, tris-glycine |
| | Aminosugar | eg. D-glucosamine, D-galactosamine. |
| | EGF | |
| | Somatostatin analogs octreotide | |
| | Gold nanoparticle (n=1-6), nanotubes, nanoparticles | 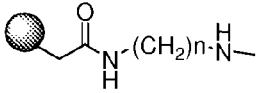 |
| | Aliphatic and aromatic N-sulfonylamides | eg. $-NH-\overset{O}{\underset{O}{S}}-CH_3$ ; $-HN-\overset{O}{\underset{O}{S}}-\text{Ph}$ |
FIG. 8

COMPOSITIONS FOR TARGETED IMAGING AND THERAPY

CROSS-REFERENCE TO RELATED APPLICATIONS

This application claims priority to U.S. provisional patent application 60/908,332, filed Mar. 27, 2007. The contents of U.S. provisional patent application 60/908,332 are incorporated by reference as though fully disclosed herein.

TECHNICAL FIELD

The present invention relates to the field of radiochemistry, nuclear imaging, radionuclide therapy and chemical synthesis. More particularly, it concerns a strategy for radiolabeling target ligands. It further concerns methods of using those radiolabeled ligands for imaging, radionuclide therapy and tissue-specific disease imaging.

BACKGROUND OF THE INVENTION

Diagnostic imaging techniques such as computed tomography (CT) and magnetic resonance imaging (MRI) provide anatomical information about disease sites. While these modalities are commonly-used for monitoring changes in tumor size, they cannot assess functional changes occurring within cells or tumors. As a result, functional imaging techniques such as Positron Emission Tomography (PET) and Single Photon Emission Computed Tomography (SPECT) have been experiencing explosive growth due to advances in molecular imaging technology. New molecular imaging targets for diagnosis and therapy have been developed to visualize disease states and pathological processes without surgical exploration of the body. In particular, targeted radiopharmaceuticals offer promising capabilities for the non-invasive assessment of the pathophysiology of diseases. Schillaci, O. & Simonetti, G., Cancer Biother. Radiopharm. 19: 1-10 (2004); Paulino, et al, Semin. Nucl. Med. 33: 238-43 (2003). However, radiopharmaceuticals suitable for clinical use have been limited, which has led to the recent development of new radiopharmaceuticals with improved sensitivity, specificity, signal-to-background ratio and biodistribution. Srivastava, S. C., Semin. Nucl. Med. 26: 119-31 (1996); Gatley, et al, Acta. Radiol. Suppl. 374: 7-11 (1990); Mason, N. S. & Mathis, C. A., Neuroimaging Clin. N. Am. 13, 671-87 (2003).

PET is a non-invasive medical imaging technology that can generate high-resolution images of human and animal physiologic functions. Its clinical applications include oncology, cardiology and neurology. PET imaging can be very effective in the detection of disease as well is in the treatment planning and treatment follow-up phases, respectively. The medical importance of PET imaging is due to the availability of multiple radiotracers which are composed of the cyclotron-produced radioisotopes: $^{11}C$, $^{13}N$, $^{15}O$ and $^{18}F$.

Radioisotopes are often created by a cyclotron or via a generator-based synthesis protocol. Cyclotrons are large and costly systems, and as a result, many medical imaging facilities must obtain their radioisotopes from cyclotron facilities that are significant distances away. The time that it takes to synthesize a radiopharmaceutical, and then deliver it to a medical imaging facility necessitates that the radioisotopes used have somewhat longer half-lives than might otherwise be ideal.

While FDG-PET is an effective marker for metabolic imaging, limited accessibility and high cost have encouraged imaging research to broaden the diagnostic capabilities of PET. Currently, investigators can use generators based on a parent-daughter (P/D) nuclidic pairing, wherein a relatively long-lived parent isotope (obtained from a cyclotron) decays to a short-lived daughter isotope better suited for imaging. The parent isotope can be shipped to a clinical site and act as the source from which the daughter isotope can be readily eluted. Generators of this type are generally smaller and relatively inexpensive and therefore, are more readily affordable for use on-site at medical imaging facilities.

Commonly used cyclotron-produced radionuclides (i.e. $^{11}C$, $^{13}N$, $^{15}O$ and $^{18}F$) are covalently linked to targeting molecules and do not require the use of a chelating moiety. This is in contrast with generator-produced radionuclides, which are typically radiometals, and use coordination chemistry through the presence of a chelator for radiolabeling. Chelators which bind radiometals and are conjugated to biomolecules are referred to as bifunctional chelating agents (BFCAs). Electron-rich atoms such as nitrogen, oxygen, sulfur and phosphorus comprise the coordinating portion of most BFCAs. Common BFCAs for radiometallic chelation include DTPA, hydrazinonicotinamide (HYNIC), mercaptoacetyltriglycine (MAG3), tetraaza compounds (i.e. 1,4,7, 10-tetraazacyclododecane-1,4,7,10-tetraacetic acid [DOTA] and macrocyclic derivatives) and ethylenedicysteine (EC). Each BFCA possesses various combinations of electron-donating atoms for metal chelation.

The selection and conjugation of BFCAs to biomolecules are carefully designed to produce minimal structural alterations to avoid disturbing the targeting activity of the ligand. BFCAs serve two main purposes: 1) to coordinate the radiometal and 2) to provide a molecular backbone that can be modified with functional groups for attachment to the targeting biomolecule. Conjugation of a BFCA to a biomolecule will alter the physical and biological characteristics of the biomolecule. BFCAs such as DTPA will dramatically increase the hydrophilic character of a biomolecule and lead to increased renal excretion. Macrocyclics (e.g., tetraaza chelators), on the other hand, can be modified to obtain suitable pharmacokinetics allowing for conjugation to both lipophilic and hydrophilic ligands, and are capable of chelating a variety of radionuclides.

Improvement of scintigraphic tumor diagnosis, prognosis, planning, and monitoring of treatment of cancer is intimately linked with the development of more tumor-specific radiopharmaceuticals. The application of molecular targets for cancer imaging, therapy, and prevention is the major focus of molecular imaging research. The use of PET and SPECT for tumor characterization is being enhanced through the development of novel radiolabeled ligands, antibodies, and therapeutic agents. As a result, molecular nuclear medicine is improving methodologies for the monitoring of tumor response to treatment, differential diagnosis, and prediction of therapeutic response through the development and characterization of novel radiotracers.

Similarly, therapeutic nuclear medicine has benefited from the discovery and validation of novel molecular targets. Identifying specific molecules associated with certain diseases has lead to the development of targeted biomolecules which carry a therapeutic radionuclide as a payload. This results in specific delivery of radioactivity to the desired site while sparing non-target organs from unnecessary radiation dose. $^{90}Y$ is a beta-emitting radioisotope which has been used clinically for radionuclide therapy. A major concern with this approach is renal toxicity associated with $^{90}Y$ and has lead to a shift in the field towards using different therapeutic radionuclides. Also, although extensive clinical and preclinical studies have been undertaken with different $^{90}$Y-molecules, one major drawback exists: it is a pure beta emitter and must therefore use $^{111}$In as a "matching pair" surrogate for imaging, biodistribution and assessing dosimetry. Many assumptions are made using this technique, therefore, much attention has been directed towards practical application of therapeutic radionuclides that also have imaging capabilities for more accurate dosimetry calculations. Incorporating such radionuclides into targeted biomolecules capable of radiometal chelation can provide the opportunity to selectively deliver radiation to a specific site for either diagnostic or therapeutic purposes.

The present invention overcomes limitations in regards to the availability of PET imaging in sites without a nearby cyclotron, the lack of targeted radionuclide therapy and other drawbacks of the prior art by providing a new radiolabeling strategy to target tissues for imaging. The invention provides versatile drug conjugates which can be labeled with various radioactive and non-radioactive metals and possess tissue-specific ligands, as well as methods for making the radiolabeled ligands and for using them to image and treat tissue-specific diseases.

BRIEF SUMMARY OF THE INVENTION

The present invention is directed to the field of radiochemistry, nuclear imaging, radionuclide therapy, drug development and chemical synthesis. More particularly, it concerns a strategy for radiolabeling target ligands. It further concerns methods of using those radiolabeled ligands for imaging, radionuclide therapy and tissue-specific disease imaging.

In one aspect of the present invention there is a composition comprising a TA2S derivative conjugated to a therapeutic or diagnostic ligand and optionally chelated to a metal, wherein said TA2S derivative has the general formula:

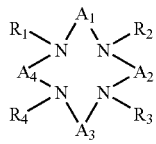

wherein $A_1$, $A_2$, $A_3$, and $A_4$ may be the same or different and are selected from the group consisting of $C_2$-$C_4$ alkyl, $C_2$-$C_4$ alkenyl, $C_2$-$C_4$ alkynyl, and any combination thereof; and, wherein one of ($R_1$ and $R_3$), or ($R_2$ and $R_4$) are the same or different and are hydrogen or a ligand, and the other of ($R_1$ and $R_3$), or ($R_2$ and $R_4$) are —$(CH_2)_n$—C(O)—R', wherein each R' group is the same or different from the other R' group and is either a hydroxyl group or a ligand; and wherein n=1-4.

In another embodiment of the composition, $A_1$, $A_2$, $A_3$, and $A_4$ are each —($CH_2$—$CH_2$)— groups and having the following structure:

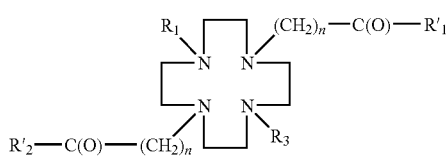

wherein ($R_1$ and $R_3$) are the same or different and are hydrogen or a ligand and ($R_1$' and $R_2$') are the same or different and are a ligand or a hydroxyl group, and wherein n=1-4, and said TA2S derivative is a DO2S derivative.

In another embodiment, the composition has the following structure:

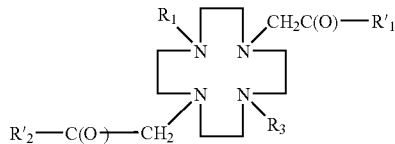

(a) ($R_1$ and $R_3$) are hydrogen and ($R_1$' and $R_2$') are the same or different and are a ligand or hydroxyl group; or, (b) ($R_1$ and $R_3$) are ligands and ($R_1$' and $R_2$') are the same or different and are a ligand or hydroxyl group; and, and said DO2S derivative is a DO2S derivative-1.

In one embodiment of the DO2S derivative composition, the ligand is selected from the group consisting of a proliferation targeting ligand, an angiogenesis targeting ligand, a tumor apoptosis targeting ligand, a disease receptor targeting ligand, a drug-based ligand, a microbial agent, a glucose-mimicking agent, a hypoxia targeting agent, an extracellular matrix targeting ligand, and any combination thereof. In one embodiment of the DO2S derivative composition, the DO2S derivative further comprises at least one linker, wherein said at least one linker forms a link to conjugate said DO2S derivative to said targeting ligand. In an embodiment comprising at least one linker, the at least one linker is selected from the group consisting of ethylenediamine, amino propanol, diethylenetriamine, aspartic acid, polyaspartic acid, glutamic acid, polyglutamic acid, lysine, polyethylene glycols, and any combination thereof. In one embodiment of the DO2S derivative composition, the ligand is selected from the group consisting of glucosamine, tetraacetate mannose, octreotide, Hedgehog ligands, EGFR targeting molecules, nucleotides, nucleosides, cholesterol, estradiol, nanoparticles, carbon nanotubes, and any combination thereof. In one embodiment of the DO2S derivative composition, the ligand is an anti-cancer compound. In one embodiment of the DO2S derivative composition, the ligand is a carbohydrate. In one embodiment of the DO2S derivative composition, the DO2S derivative is chelated to a metal species. In one embodiment of the DO2S derivative composition chelated to a metal species, the metal species is copper, cobalt, platinum, iron, arsenic, rhenium, or germanium. In one embodiment of the DO2S derivative composition is chelated to a metal species, the metal species is a radionuclide. In one embodiment of the DO2S derivative composition is chelated to a radionuclide, the radionuclide is $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi or $^{225}$Ac.

In another embodiment, the radionuclide is $^{68}$Ga or $^{177}$Lu. In one embodiment of the DO2S derivative composition, the ligand comprises a drug.

In another aspect of the present invention, there is a method for the treatment or diagnosis of a medical condition in a subject comprising:

administering to a subject a composition comprising a TA2S derivative conjugated to a therapeutic or diagnostic ligand and optionally chelated to a metal, wherein said TA2S derivative has the general formula:

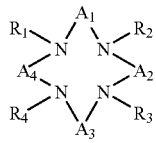

wherein $A_1$, $A_2$, $A_3$, and $A_4$ may be the same or different and are selected from the group consisting of $C_2$-$C_4$ alkyl, $C_2$-$C_4$ alkenyl, $C_2$-$C_4$ alkynyl, and any combination thereof; and, wherein one of ($R_1$ and $R_3$), or ($R_2$ and $R_4$) are the same or different and are hydrogen or a ligand, and the other of ($R_1$ and $R_3$), or ($R_2$ and $R_4$) are —$(CH_2)_n$—C(O)—R', wherein each R' group is the same or different from the other R' group and is either a hydroxyl group or a ligand; and wherein n=1-4, and, optionally imaging said subject.

In another embodiment of the method for treatment or diagnosis, $A_1$, $A_2$, $A_3$, and $A_4$ are each —$(CH_2$—$CH_2)$— groups and having the following structure:

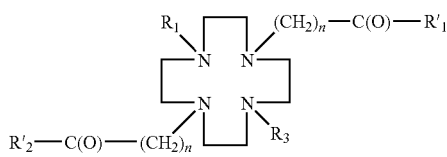

wherein ($R_1$ and $R_3$) are the same or different and are hydrogen or a ligand and ($R_1'$ and $R_2'$) are the same or different and are a ligand or a hydroxyl group, and wherein n=1-4, and said TA2S derivative is a DO2S derivative.

In another embodiment, the c method for the treatment or diagnosis has the following structure:

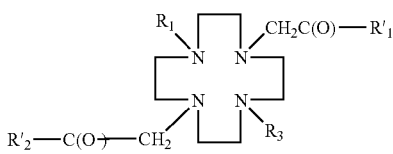

a) ($R_1$ and $R_3$) are hydrogen and ($R_1'$ and $R_2'$) are the same or different and are a ligand or hydroxyl group; or, (b) ($R_1$ and $R_3$) are ligands and ($R_1'$ and $R_2'$) are the same or different and are a ligand or hydroxyl group; and, and said DO2S derivative is a DO2S derivative-1.

In one embodiment of the method for treatment or diagnosis, the subject is a mammal. In another embodiment, the subject is a human. In one embodiment of the method for treatment or diagnosis using a DO2S derivative, the DO2S derivative is chelated to a metal species. In another embodiment, the metal species is a radionuclide. In some embodiments, the radionuclide is $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi or $^{225}$Ac. In other embodiments, the radionuclide is $^{68}$Ga or $^{177}$Lu. In some embodiments of the method wherein the DO2S derivative is chelated to a metal species, the metal species is selected from the group consisting of divalent ions of: an element of atomic number 21 to 29, 42, 44, and 57 to 83; and, trivalent ions of an element of atomic number 21 to 29, 42, 44, and 57 to 83. In one embodiment of the method for treatment or diagnosis using a DO2S derivative, the method further comprises administering radiation therapy or surgery. In one embodiment of the method for treatment or diagnosis using a DO2S derivative, the medical condition is cancer and said ligand is an anti-cancer compound. In some embodiments of the method wherein the medical condition is cancer and said ligand is an anti-cancer compound, the method further comprises administration of a second anti-cancer compound. In one embodiment of the method for treatment or diagnosis using a DO2S derivative, the ligand is selected from the group consisting of a proliferation targeting ligand, an angiogenesis targeting ligand, a tumor apoptosis targeting ligand, a disease receptor targeting ligand, a drug-based ligand, a microbial agent, a glucose-mimicking agent, a hypoxia targeting agent, an extracellular matrix targeting ligand, and any combination thereof. In one embodiment of the method for treatment or diagnosis using a DO2S derivative, the DO2S derivative further comprises at least one linker, wherein said at least one linker forms a link to conjugate said DO2S derivative to said targeting ligand. In some embodiments of the methods using at least one linker, the at least one linker is selected from the group consisting of ethylenediamine, amino propanol, diethylenetriamine, aspartic acid, polyaspartic acid, glutamic acid, polyglutamic acid, lysine, polyethylene glycols, and any combination thereof. In one embodiment of the method for treatment or diagnosis using a DO2S derivative, the ligand is selected from the group consisting of glucosamine, tetraacetate mannose, octreotide, hyaluronic acid, Hedgehog ligands, EGFR targeting molecules, nucleotides, nucleosides, cholesterol, estradiol, nanoparticles, carbon nanotubes, and any combination thereof. In one embodiment of the method for treatment or diagnosis using a DO2S derivative, the ligand is an anti-cancer compound. In one embodiment of the method for treatment or diagnosis using a DO2S derivative, the ligand is a carbohydrate.

In another aspect of the present invention, there is a kit for the treatment or diagnosis of a medical condition in a subject comprising, said kit comprising a composition comprising a TA2S derivative conjugated to a therapeutic or diagnostic ligand and optionally chelated to a metal, wherein said TA2S derivative comprises the general formula:

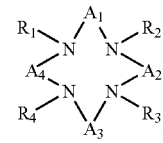

wherein $A_1$, $A_2$, $A_3$, and $A_4$ may be the same or different and are selected from the group consisting of $C_2$-$C_4$ alkyl, $C_2$-$C_4$ alkenyl, $C_2$-$C_4$ alkynyl, and any combination thereof; and, wherein one of ($R_1$ and $R_3$), or ($R_2$ and $R_4$) are the same or different and are hydrogen or a ligand, and the other of ($R_1$ and $R_3$), or ($R_2$ and $R_4$) are —$(CH_2)_n$—C(O)—R', wherein each R' group is the same or different from the other R' group and is either a hydroxyl group or a ligand; and wherein n=1-4.

In another embodiment of the kit, $A_1$, $A_2$, $A_3$, and $A_4$ are each —$(CH_2$—$CH_2)$— groups and having the following structure:

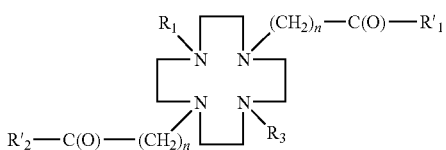

wherein ($R_1$ and $R_3$) are the same or different and are hydrogen or a ligand and ($R_1'$ and $R_2'$) are the same or different and are a ligand or a hydroxyl group, and wherein n=1-4, and said TA2S derivative is a DO2S derivative.

In one embodiment of the kit wherein the composition comprises a DO2S derivative, the DO2S derivative has the following structure:

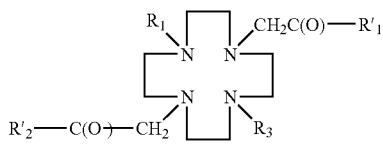

a) ($R_1$ and $R_3$) are hydrogen and ($R_1'$ and $R_2'$) are the same or different and are a ligand or hydroxyl group; or, (b) ($R_1$ and $R_3$) are ligands and ($R_1'$ and $R_2'$) are the same or different and are a ligand or hydroxyl group; and, and said DO2S derivative is a DO2S derivative-1.

In one embodiment of the kit having a composition comprising a DO2S derivative, the metal species is a radionuclide. In some embodiments, the radionuclide is $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi or $^{225}$Ac. In some embodiments, the radionuclide is $^{68}$Ga or $^{177}$Lu. In some embodiments of the kit having a composition comprising a DO2S derivative, the kit further comprises an antioxidant. In some embodiments having an antioxidant, the antioxidant is vitamin C, gentisic acid, tocopherol, pyridoxine, thiamine, or rutin. In some embodiments, the kit further comprises a transchelator. In some embodiments having a transchelator, the transchelator is glucoheptonate, gluconate, glucarate, citrate, tartarate, DOTA, diethylenetriaminepentaacetic acid, or ethylenediaminetetraacetic acid. In some embodiments, the kit further comprises a reducing agent. In some embodiments having a reducing agent, the reducing agent is tin (II) chloride or triphenylphosphine. In some embodiments of the kit having a composition comprising a DO2S derivative, the ligand is a tumor targeting ligand. In some embodiments of the kit having a composition comprising a DO2S derivative, the ligand is selected from the group consisting of a proliferation targeting ligand, an angiogenesis targeting ligand, a tumor apoptosis targeting ligand, a disease receptor targeting ligand, a drug-based ligand, a microbial agent, a glucose-mimicking agent, a hypoxia targeting agent, an extracellular matrix targeting ligand, and any combination thereof. In some embodiments of the kit having a composition comprising a DO2S derivative, the DO2S derivative further comprises at least one linker, wherein said at least one linker forms a link to conjugate said DO2S derivative to said targeting ligand. In some embodiments having at least one linker, the at least one linker is selected from the group consisting of ethylenediamine, amino propanol, diethylenetriamine, aspartic acid, polyaspartic acid, glutamic acid, polyglutamic acid, lysine, polyethylene glycols, and any combination thereof. In some embodiments of the kit having a composition comprising a DO2S derivative, the ligand is selected from the group consisting of glucosamine, tetraacetate mannose, octreotide, hyaluronic acid, Hedgehog ligands, EGFR targeting molecules, nucleotides, nucleosides, cholesterol, estradiol, nanoparticles, carbon nanotubes, and any combination thereof. In some embodiments of the kit having a composition comprising a DO2S derivative, the ligand is an anti-cancer compound. In some embodiments of the kit having a composition comprises a DO2S derivative, the ligand is a carbohydrate.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which: ZZZ FIG. 1a-1c illustrates synthetic pathways for DO2S derivative and schematic structures of DO2S derivative 1; FIG. 1d provides a table of various ligands and coupling agents.

FIG. 2 illustrates the preparation of the mono- and di-aminosugar-containing DO2S derivative-1 labeled with radiometals.

FIGS. 5a and 5b illustrates the preparation of the dual isotope labeled of DO2S derivative-1; DO2S derivative-1 conjugated to aliphatic and aromatic amines, amino acids, polyamines.

FIG. 6 illustrates the preparation of DO2S-phosphate and phosphorothioate modified with lipophylic ligand.

FIG. 8 illustrates the modification of DO2S derivative-1 at the N-4 and/or N-10 position.

DETAILED DESCRIPTION OF THE INVENTION

Figure 3A:
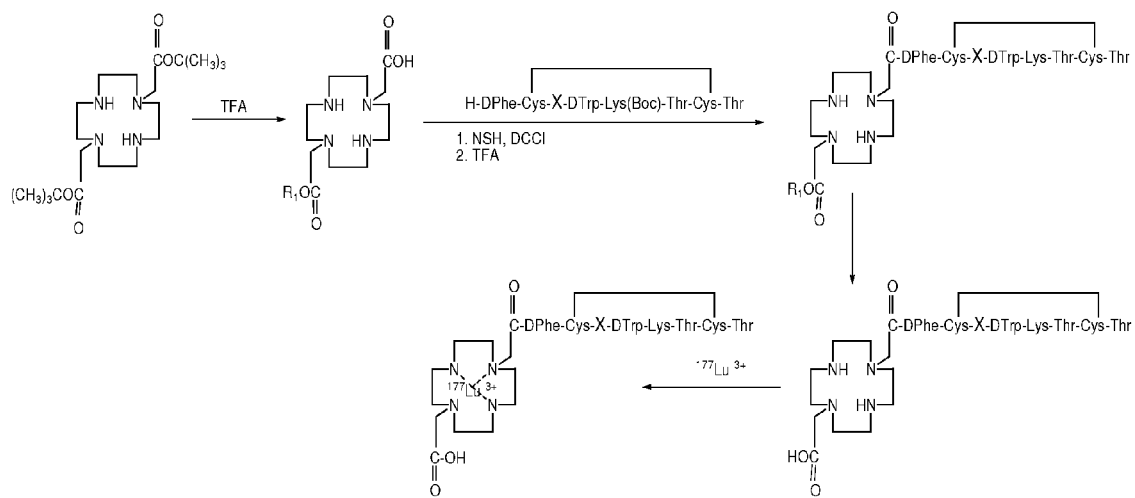
FIG. 3a illustrates the preparation of DO2S derivatives containing somatostatin analogs labelled with radiometals.

As used herein, "a" and "an" include both the singular and the plural and mean one or more than one. For example, "a ligand" means one ligand or more than one ligand.

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

An "alkyl" group refers to a saturated aliphatic hydrocarbon, including straight-chain, branched chain, and cyclic alkyl groups. Alkyl groups can comprise any combination of acyclic and cyclic subunits. Further, the term "alkyl" as used herein expressly means an unbranched or branched hydrocarbon chain having single bonds therein. The alkyl group may be substituted or unsubstituted. When substituted, the substituted group(s) may be hydroxyl, cyano, alkoxy, =O, =S, $-NO_2$, $-N(CH_3)_2$, amino, or $-SH$. Preferably, the alkyl group has 1 to 12 carbons. More preferably, it is a lower alkyl of from 1 to 7 carbons, more preferably 2 to 4 carbons, more preferably selected from the group consisting of $-CH_2-CH_2-$, $-CH_2-CH_2-CH_2-$, and $-CH_2-CH_2-CH_2-CH_2-$.

An "alkenyl" group means an unbranched or branched hydrocarbon chain having one or more double bonds therein. The "alkenyl" groups can be unsubstituted or substituted with one or more groups. When substituted, the substituted group(s) may be hydroxy, cyano, alkoxy, chloro, bromo, iodo, amino, thiolo. Preferably, the alkenyl group has 2 to 4 carbons, more preferably selected from the group consisting of $-CH=CH-$, $-CH_2-CH=CH-$, $-CH=CH-CH_2-$, $-CH_2-CH=CH-CH_2$, $-CH=CH-CH=CH-$. The term "alkenyl" groups include groups such as pentenyl, hexenyl, pentadienyl, hexadienyl.

An "alkynyl" group means an unbranched or branched hydrocarbon chain having one or more triple bonds therein. The "alkynyl" groups can be unsubstituted or substituted with one or more groups. When substituted, the substituted group(s) may be hydroxy, cyano, alkoxy, chloro, bromo, iodo, amino, thiolo. Preferably, the alkynyl group has 2 to 4 carbons, more preferably selected from the group consisting of $-C\equiv C-$, $-CH_2-C\equiv C-$, $-C\equiv C-CH_2-$, $-CH_2-C\equiv C-CH_2$, $-C\equiv C-CH=CH_2-$. The term "alkynyl" groups include groups such as pentynyl, hexynyl, pentadiynyl, hexadiynyl.

As used herein, the word "compound" means a free chemical molecular entity or a chemical moiety that is part of a larger molecular entity. Therefore, when reference is made, for example, to a targeting ligand being an anti-cancer compound, the language encompasses both an anti-cancer compound moiety incorporated within a larger chemical entity as well as the free anticancer compound.

The word "conjugate" and "conjugated" is defined herein as chemically joining within the same molecule. For example, two or more molecules and/or atoms may be conjugated together via a covalent bond, forming a single molecule. The two molecules may be conjugated to each other via a direct connection (e.g., where the compounds are directly attached via a covalent bond) or the compounds may be conjugated via an indirect connection (e.g., where the two compounds are covalently bonded to one or more linkers, forming a single molecule). In other instances, a metal atom may be conjugated to a molecule via a chelation interaction.

In one aspect of the present invention, there is a therapeutic and/or diagnostic composition, the composition comprising a tetraaza compound (or any subgenus as defined below) conjugated to a ligand, the tetraaza compound optionally chelated to a metal species. The ligand may be a drug or targeting biomolecule or other therapeutic or diagnostic ligand. A tetraaza compound is defined herein as compound comprising the structure:

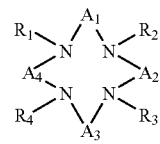

wherein $A_1$, $A_2$, $A_3$, and $A_4$ may be the same or different and are selected from the group consisting of $C_2$-$C_4$ alkyl, $C_2$-$C_4$ alkenyl, $C_2$-$C_4$ alkynyl, and any combination thereof; and, wherein ($R_1$-$R_4$) are the same or different and are hydrogen or the following group: $-(CH_2)_n-C(O)OR'$, wherein n=1-4 wherein the OR' is a protecting group that is replaced by the ligand to form the therapeutic and/or diagnostic composition. In the case where any given R group of ($R_1$-$R_4$) is not hydrogen, that R group position is said to be substituted. Where three R groups are hydrogen and one R group is non-hydrogen, the compound is mono-substituted. Where two R groups are hydrogen and the other two R groups are non-hydrogen, the compound is di-substituted, etc. Preferably, the substitutions are the same and R' is selected from the group consisting of methyl, 2-chloroethyl, 2-bromoethyl, 2-iodoethyl, ethyl, allyl, heptyl, 2-N-(morpholino)ethyl, 2,2,2-trifluoroethyl, 2,2,2-trichloroethyl, 2-cyanoethyl, ω-chloroalkyl, t-butyl, benzyl, benzhydryl, phenacyl, p-bromophenacyl, α-methylphenacyl, p-methoxyphenacyl, acetol, phenylacetoxymethyl, desyl, diphenylmethyl, 1,3-dithianyl-2-methyl, o-nitrobenzyl, p-nitrobenzyl, carboxamidomethyl, p-azobenzene-carboxamidomethyl, N-phthalimidomethyl, trimethylsilyl, triethylsilyl, triisopropyl-silylmethyl, triisopropylsilyl, t-butyldiphenylsilyl, t-butyldimethylsilyl, isopropyldimethylsilyl, phenyldimethylsilyl, di-t-butylmethylsilyl, cyanomethyl, methoxymethyl, methoxyethyl, β-methoxyethoxymethyl, methylthiomethyl, methylthioethyl, p-(methylthio)phenyl, benzyloxymethyl, tetrahydrofuranyl, tetrahydropyranyl, pivaloyloxymethyl, phenyl, 2-(trimethyl-silyl)ethoxymethyl, trimethylsilyl, 2-(trimethylsilyl)ethyl, 2-(p-toluenesulfonyl)ethyl, 2-(p-nitrophenylsulfenyl)ethyl, 2-(2'-pyridyl)ethyl, 2-(p-methoxy-phenyl)ethyl, 1-methyl-1-phenylethyl, 2-(4-acetyl-2-nitrophenyl)ethyl, 3-methyl-3-pentyl, dicyclopropylmethyl, 2,4-dimethyl-3-pentyl, cyclopentyl, cyclohexyl, 2-methyl-but-3-en-2-yl, 3-methylbut-2-prenyl, 3-buten-1-yl, 4-(trimethylsilyl)-2-buten-1-yl, cinnamyl, prop-2-ynyl, 2,6-dimethylphenyl, 2,6-diidopropylphenyl, 2,6-di-t-butyl-methylphenyl, 2,6-di-t-butyl-4-methoxyphenyl, pentafluorophenyl, triphenylmethyl, bis-(o-nitrophenylmethyl), 9-anthrylmethyl, 2-(9,10-dioxo)anthrylmethyl, 5-benzosuberyl, 1-pyrenylmethyl, 2-(trifluoromethyl)-6-chromonylmethyl, 2,4,6-trimethylbenzyl, p-bromobenzyl, p-methoxybenzyl, 4-(methylsylfinyl)benzyl, 4-sulfobenzyl, 4-azido-methoxybenzyl, 4-{N-[1-(4,4-dimethyl-2,6-dioxocyclohexylidene)-3-methylbutyl]-amino}benzyl, piperonyl, 4-picolyl, p-benzyl, 9-fluorenylmethyl, methallyl, α-methylcinnamyl, and any combination thereof. Tetraaza compounds are characterized, in part, by the presence of four nitrogen atoms in a ring system and can also be referred as N4 compounds. In the chemical formula $-(CH_2)_n-C(O)OR'$, it should be understood that the oxygen atom in the parentheses is a carbonyl oxygen bonded by a double bond to the adjacent carbon, while the other oxygen atom is bonded by a single bond to the same carbon atom and to the R' group forming an ester group. Where there is more than one protecting group, the R' groups can be the same or different. The OR' is a protecting group that is replaced by a ligand to form the therapeutic and/or diagnostic composition. Thus, the term "tetraaza compound conjugated to a ligand", means either a tetraaza compound with one or more of its OR' groups replaced by a ligand, or if the tetraaza compound has all $R_1$-$R_4$ as hydrogen, then one or more of said hydrogens is replaced by a ligand.

The term "TA2S derivative" refers to a class of compounds which is a subgenus of tetraaza compounds. In another embodiment, there is a composition comprising a TA2S derivative conjugated to a ligand and optionally chelated to a metal, wherein said TA2S derivative has the general formula:

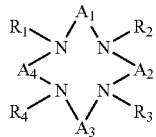

wherein $A_1$, $A_2$, $A_3$, and $A_4$ may be the same or different and are selected from the group consisting of $C_2$-$C_4$ alkyl, $C_2$-$C_4$ alkenyl, $C_2$-$C_4$ alkynyl, and any combination thereof; and, wherein one of ($R_1$ and $R_3$), or ($R_2$ and $R_4$) are hydrogen and the other of ($R_1$ and $R_3$), or ($R_2$ and $R_4$) are —($CH_2$)$_n$—C(O)—OR'; wherein n=1-4. R' is as defined above for tetraaza compounds. The OR' is a protecting group that is replaced by a ligand to form a therapeutic and/or diagnostic composition. Thus, the term "TA2S derivative conjugated to a ligand", means either a TA2S derivative with one or more of its OR' groups or one or more of its hydrogens is replaced by a ligand.

In some embodiments of the composition, $A_1$, $A_2$, $A_3$, and $A_4$ are each —($CH_2$—$CH_2$)— groups and said TA2S derivative is a DO2S derivative. DO2S derivatives are a class of compounds and are a subgenus of TA2S derivatives. The term "DO2S derivative conjugated to a ligand", means either a DO2S derivative with one or more of its OR'$_1$ or OR'$_2$ groups or one or more of its hydrogens is replaced by a ligand (with reference to the structures below).

A general structure covering DO2S derivatives and DO2S derivatives conjugated to a ligand is as follows:

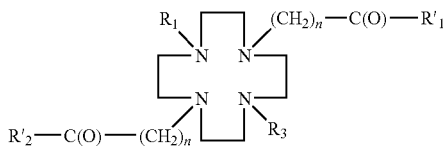

wherein n=1-4 and (a) ($R_1$ and $R_3$) are hydrogen and (R'$_1$ and R'$_2$) are the same or different and are ligands or hydroxyl; or (b) ($R_1$ and $R_3$) are the same or different and are ligands or hydrogen and (R'$_1$ and R'$_2$) are the same or different and are ligands or hydroxyl groups.

In some embodiments of the DO2S derivative, $R_1$ and $R_3$ are hydrogen, n=1, and said DO2S derivative is a DO2S derivative-1. A DO2S derivative-1 is a class of compounds and is a subgenus of DO2S derivatives. A general structure covering DO2S derivative-1 and DO2S derivative-1 conjugated to a ligand is as follows (with R'$_1$ and R'$_2$ as defined above):

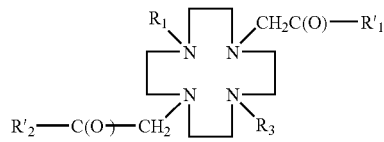

DO2S derivative-1 is a class of compounds and is a subgenus of DO2S derivatives. The tetraaza compound may comprise a DO2S compound that is conjugated to a targeting ligand (via a covalent bond) and/or a linker (via a covalent bond) and/or a metal chelate (via a chelation interaction). Both DO2S and DO2S derivative-1 are subgenera of tetraaza compounds; DO2S derivatives are a sub-genus of tetraaza compounds. The tetraaza compounds, TA2S derivatives, and DO2S derivatives described herein, when used in the compositions, methods, and kits of the present inventions are the macrocycles (of macrocyclic compounds) of the present invention.

In other aspects of the invention, the above compositions are used in the preparation of a diagnostic or therapeutic composition. The diagnostic or therapeutic compositions include kits for use in treatment or diagnosis of a medical condition. The following are non-limiting examples of various embodiments of the kit. In preferred embodiments of the kit, the composition is a DO2S derivative chelated to a metal. The metal is a radionuclide in some embodiments. Examples of radionuclide is $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi or $^{225}$Ac. The radionuclide is preferably $^{68}$Ga or $^{177}$Lu. The kit may further comprise an antioxidant such as vitamin C, getistic acid, tocopherol, pyridoxine, thiamine, or rutin. The kit may comprise a transchelator, such as glucoheptonate, gluconate, glucarate, citrate, tartarate, DOTA, diethylenetriaminepentaacetic acid, or ethylenediaminetetraacetic acid. The kit may comprise a reducing agent, such as tin (II) chloride or triphenylphosphine. The ligand may be a tumor targeting ligand. Other examples of the ligand include, but are not limted to, a proliferation targeting ligand, an angiogenesis targeting ligand, a tumor apoptosis targeting ligand, a disease receptor targeting ligand, a drug-based ligand, a microbial agent, a glucose-mimicking agent, a hypoxia targeting agent, an extracellular matrix targeting ligand, and any combination thereof. The kit may further comprise at least one linker, wherein the at least one linker forms a link to conjugate said DO2S derivative to the targeting ligand. Non-limiting examples of the at least one linker include ethylenediamine, amino propanol, diethylenetriamine, aspartic acid, polyaspartic acid, glutamic acid, polyglutamic acid, lysine, polyethylene glycols, and any combination thereof. Other non-limiting examples of the ligand include glucosamine, tetraacetate mannose, octreotide, hyaluronic acid, Hedgehog ligands, EGFR targeting molecules, nucleotides, nucleosides, cholesterol, estradiol, nanoparticles, carbon nanotubes, and any combination thereof. In some embodiments, the ligand is an anti-cancer compound. In some embodiments, the ligand is a carbohydrate.

As used herein the term "radionuclide" is defined as a radioactive nuclide (a species of atom able to exist for a measurable lifetime and distinguished by its charge, mass, number, and quantum state of the nucleus) which, in specific embodiments, disintegrates with emission of corpuscular or electromagnetic radiation. The term may be used interchangeably with the term "radioisotope".

The term "therapeutic agent" as used herein is defined as an agent which provides treatment for a disease or medical condition. The agent in a specific embodiment improves at least one symptom or parameter of the disease or medical condition. For instance, in tumor therapy, the therapeutic agent reduces the size of the tumor, inhibits or prevents growth or metastases of the tumor, or eliminates the tumor. Examples include a drug, such as an anticancer drug, a gene therapy composition, a radionuclide, a hormone, a nutriceutical, or a combination thereof. The therapeutic agent may be a ligand on a tetraaza compound, or on TA2S or DO2S derivatives.

The term "tumor" as used herein is defined as an uncontrolled and progressive growth of cells in a tissue. A skilled artisan is aware other synonymous terms exist, such as neoplasm or malignancy. In a specific embodiment, the tumor is a solid tumor. In other specific embodiments, the tumor derives, either primarily or as a metastatic form, from cancers such as of the liver, prostate, pancreas, head and neck, breast, brain, colon, adenoid, oral, skin, lung, testes, ovaries, cervix, endometrium, bladder, stomach, and epithelium.

The term "drug" as used herein is defined as a compound which aids in the treatment of disease or medical condition or which controls or improves any physiological or pathological condition associated with the disease or medical condition.

The term "anticancer drug" as used herein is defined as a drug for the treatment of cancer, such as for a solid tumor. The anticancer drug preferably reduces the size of the tumor, inhibits or prevents growth or metastases of the tumor, and/or eliminates the tumor. The terms "anticancer drug", "anticancer drug", and "anti-cancer compound" are used interchangeably herein.

As used herein the specification, "a" or "an" may mean one or more. As used herein in the claim(s), when used in conjunction with the word "comprising", the words "a" or "an" may mean one or more than one. As used herein "another" may mean at least a second or more.

I. Tetraaza Compounds, TA2S Derivatives, and DO2S Derivatives

The present invention provides a method by which tetraaza compounds (or any subgenus as defined herein) which are chelators, may be conjugated to drugs or biomolecules to produce novel compounds which may be used for purposes including imaging and radiotherapy. The tetraaza compound is preferably a TA2S, more preferably a DO2S derivative, and most preferably DO2S derivative-. Compounds and starting materials for their synthesis may be obtained from commercial source such as Macrocyclics (Dallas, Tex.). U.S. Pat. No. 5,880,281 describes a method for producing certain tetraazamacrocyclic compounds and is incorporated by reference as though fully disclosed herein. In the remainder of the discussion herein, wherever reference is made to any of one or more of 1) tetraaza compounds, 2) TA2S derivatives, 3) DO2S derivatives, or 4) DO2S derivative-1, the discussion is also applicable to and should be understood to be applicable to, any of the other aforementioned groups of compounds. Tetraaza compounds, TA2S derivatives, and DO2S derivatives are all macrocycles.

Tetraaza compounds (as well as any subgenus or species thereof) can be used as chelators. For example, cyclam and other tetraaza compounds were tested for their ability to alleviate acute cadmium poisoning (Srivastava et al., 1996). U.S. Pat. No. 4,141,654 describes certain compounds with structural similarity to tetraaza compounds that may be used to chelate actinide ions. U.S. Pat. No. 5,648,063 discloses compounds with structural similarity to tetraaza compounds which can chelate metal ions and may also be used in certain NMR diagnostic procedures. U.S. Pat. No. 6,071,490 utilizes a modified cyclen for PET imaging. U.S. Pat. No. 6,613,305 discloses Vitamin $B_{12}$ attached to various tetraaza compounds.

The present invention provides compositions for tissue specific disease imaging and treatment. The compositions of the invention generally include a diagnostic radionuclide chelated by a tetraaza compound (the tetraaza compound preferably being a DO2S derivative and more preferably being DO2S derivative-1) and a tissue specific ligand conjugated to the tetraaza compound. In a preferred embodiment, the tetraaza compound is DO2S derivative-1, and the tissue specific ligand is conjugated to the DO2S derivative-1 through one or two of its acid arms and/or one or both of the secondary amines. The tetraaza compound forms coordination bonds with the radionuclide. As used herein, the term "conjugate" refers to a covalently bonded compound. When a moiety is conjugated to another moiety, there is a covalent bond linking the two moieties.

DO2S derivatives (the preferred compounds of the present invention) and DO2S derivative-1 (the most preferred compound of the present invention) are tetraaza ligands. Such compounds form very stable complexes with transition metal ions and lanthanide series elements. Such chelators have been labeled with multiple radionuclides including $^{64/67}Cu$, $^{67/68}Ga$, $^{86/90}Y$, $^{111}In$ and $^{177}Lu$. Macrocyclics have also been shown to form very stable complexes with $^{99m}Tc$ on the basis of efficient binding of the oxotechnetium group to three amine-nitrogen atoms.

Tetraaza compounds have been used for chelation of multiple radionuclides for diagnostic applications. Among these, $^{68}Ga$-based PET agents ($t_{1/2}$=68 min, $\beta^+$=89% and EC=11%) possess significant research and clinical potential because the isotope can be produced from a $^{68}Ge/^{68}Ga$ generator ($t_{1/2}$=271 days) on-site and provide a convenient alternative to cyclotron-based PET isotopes. The short half-life of $^{68}Ga$ permits applications with suitable radioactivity while maintaining patient dose to an acceptable level. Furthermore, the $^{68}Ga^{3+}$ cation can form stable complexes with many ligands containing oxygen, nitrogen and sulfur as donor atoms, making it suitable for complexation with a wide range of chelators and macromolecules.

A targeting ligand is a compound that, when introduced into the body of a mammal or patient, will specifically bind to a specific type of tissue. It is envisioned that the compositions of the invention may include virtually any known tissue specific compound. Preferably, the tissue specific ligand used in conjunction with the present invention will be an anticancer agent, DNA topoisomerase inhibitor, antimetabolite, tumor marker, folate receptor targeting ligand, tumor apoptotic cell targeting ligand, tumor hypoxia targeting ligand, DNA intercalator, receptor marker, peptide, nucleotide, organ specific ligand, antimicrobial agent, such as an antibiotic or an antifungal, glutamate pentapeptide or an agent that mimics glucose. The agents that mimic glucose may also be referred to as "sugars."

Preferred anticancer agents include methotrexate, doxorubicin, tamoxifen, paclitaxel, topotecan, LHRH, mitomycin C, etoposide, tomudex, podophyllotoxin, mitoxantrone, camptothecin, colchicine, endostatin, fludarabin and gemcitabine. Preferred tumor markers include PSA, ER, PR, AFP, CA-125, CA-199, CEA, interferons, BRCA1, cytoxan, p53, VEGF, integrins, endostatin, HER-2/neu, EGF, Hedgehog molecules, antisense markers or a monoclonal antibody. It is envisioned that any other known tumor marker, therapeutic peptide, antibody fragment or any monoclonal antibody will be effective for use in conjunction with the invention. Preferred folate receptor targeting ligands include folate, methotrexate and tomudex. Preferred tumor apoptotic cell or tumor hypoxia targeting ligands include annexin V, colchicine, nitroimidazole, mitomycin or metronidazole. Preferred antimicrobials include ampicillin, amoxicillin, penicillin, cephalosporin, clidamycin, gentamycin, kanamycin, neomycin, natamycin, nafcillin, rifampin, tetracyclin, vancomycin, bleomycin, and doxycyclin for gram positive and negative bacteria and amphotericin B, amantadine, nystatin, ketoconazole, polymycin, acyclovir, and ganciclovir for fungi. Preferred agents that mimic glucose, or sugars, include neomycin, kanamycin, gentamycin, paromycin, amikacin, tobramycin, netilmicin, ribostamycin, sisomicin, micromicin, lividomycin, dibekacin, isepamicin, astromicin, aminoglycosides, glucose or glucosamine.

In certain embodiments, it will be necessary to include a linker between the 1) tetraaza compound, 2) TA2S derivative, or 3) DO2S derivative (in the present invention any one or a combination of these three groups can serve as the macrocycle and may be referred to as the macrocycle), and the tissue specific ligand. A linker is typically used to increase drug solubility in aqueous solutions as well as to minimize alteration in the affinity of drugs. While virtually any linker which will increase the aqueous solubility of the composition is envisioned for use in conjunction with the present invention, the linkers will generally be a poly-amino acid, a water soluble peptide, a single amino acid or poly(ethylene) glycols. For example, when the functional group on the tissue specific ligand, or drug, is aliphatic or phenolic-OH, such as for estradiol, topotecan, paclitaxel, raloxifene, or etoposide, the linker may be poly-glutamic acid (MW about 750 to about 15,000), poly-aspartic acid (MW about 2,000 to about 15,000), bromo ethylacetate, glutamic acid or aspartic acid. When the drug functional group is aliphatic or aromatic-$NH_2$ or peptide, such as in doxorubicin, mitomycin C, endostatin, annexin V, LHRH, octreotide, and VIP, the linker may be poly-glutamic acid (MW about 750 to about 15,000), poly-aspartic acid (MW about 2,000 to about 15,000), glutamic acid or aspartic acid. When the drug functional group is carboxylic acid or peptide, such as in methotrexate or folic acid, the linker may be ethylenediamine, or lysine.

The present inventors have also discovered that it is possible to bind a second moiety to the polypeptide, such as a tissue targeting moiety, a therapeutic moiety, or an imaging moiety, such that the agent is suitable for multimodality imaging or radiochemotherapy. Such conjugation reactions could be conducted, for example, in aqueous or organic solvent conditions. The complexing of a metal ion to the polypeptide improves water solubility of the agent, and allows for use of the agent in contrast enhancement targeted imaging.

While the preferred radionuclide for imaging is $^{68}$Ga, it is envisioned that other radionuclides may be chelated to the TA2S or DO2S derivative-tissue specific ligand conjugates, or TA2S or DO2S derivative-drug conjugates of the invention, especially for use as therapeutics. For example, useful therapeutic radionuclides are $^{59}$Fe, $^{67}$Ga, $^{89}$Sr, $^{90}$Y, $^{111}$In, $^{149}$Pm, $^{153}$Gd, $^{153}$Sm, $^{166}$Ho, $^{177}$Lu, $^{186}$Re and $^{188}$Re, with $^{177}$Lu being most preferrable. Compositions containing such therapeutic radionuclides are useful for targeted delivery of radionuclide therapy to a specific lesion in the body, such as breast cancer, ovarian cancer, prostate cancer (using for example, $^{177}$Lu-DO2S derivative-folate) and head and neck cancer (using for example, $^{177}$Lu-DO2S derivative-EGFR).

Specific embodiments of the present invention include $^{68}$Ga/$^{177}$Lu-DO2S derivative-glucose, $^{68}$Ga/Lu-DO2S derivative-glucosamine, $^{68}$Ga/$^{177}$Lu-DO2S derivative-tetraacetate mannose, $^{6}$Ga/$^{177}$Lu-DO2S derivative-EGF, $^{68}$Ga/$^{177}$Lu-DO2S derivative-octreotide, $^{68}$Ga/$^{177}$Lu-DO2S derivative-hedgehog ligands, $^{68}$Ga/$^{177}$Lu-DO2S derivative-estradiol, $^{68}$Ga/$^{177}$Lu-DO2S derivative-glutamate pentapeptide, $^{68}$Ga/$^{177}$Lu-DO2S derivative-oligonucleotides, $^{68}$Ga/$^{177}$Lu-DO2S derivative-aminoglycosides, $^{68}$Ga/$^{177}$Lu-DO2S derivative-nanoparticles, $^{68}$Ga/$^{177}$Lu-DO2S derivative-carbon nanotubes.

The present invention further provides a method of synthesizing a radiolabeled macrocycle-drug conjugate for diagnostic or therapeutic use. For example, the method includes obtaining a tissue specific ligand, admixing the ligand with DO2S derivative to obtain a DO2S derivative-tissue specific ligand derivative, and admixing the DO2S derivative-tissue specific ligand derivative with a radionuclide to obtain a radiolabeled DO2S derivative-tissue specific ligand derivative. The radionuclide is chelated to the TA2S or DO2S derivative via a coordination bond by the nitrogen and oxygen atoms. The tissue specific ligand is conjugated, as described above, to one or both acid arms of the TA2S or DO2S derivative either directly or through a linker, and/or to one or both amino groups either directly or through a linker. As required, such as in the case of $^{99m}$Tc and $^{188}$Re, a reducing agent, preferably a dithionite ion, a stannous ion or a ferrous ion, is used for radiolabeling.

The present invention further provides a method for labeling a tissue specific ligand for diagnostic, therapeutic, or prognostic use. The labeling method includes the steps of obtaining a tissue specific ligand, admixing the tissue specific ligand with a macrocycle to obtain an macrocycle-ligand drug conjugate, and reacting the drug conjugate with $^{68}$Ga or $^{177}$Lu to form a coordination bond between the macrocycle and the $^{68}$Ga or $^{177}$Lu.

For purposes of this embodiment, the tissue specific ligand may be any of the ligands described above or discussed herein. The reducing agent, which is required for $^{99m}$Tc and $^{188}$Re, may be any known reducing agent, but will preferably be a dithionite ion, a stannous ion or a ferrous ion.

In another embodiment, the present invention provides a method of imaging a site within a mammalian body. The imaging method includes the steps of administering an effective diagnostic amount of a composition comprising a radiolabeled DO2S derivative-tissue specific ligand conjugate and detecting a radioactive signal from the radiotracer localized at the site. The detecting step will typically be performed from about 10 minutes to about 4 hours after introduction of the composition into the mammalian body. Most preferably, the detecting step will be performed about 1 hour after injection of the $^{68}$Ga composition, or 24 hours after injection of the $^{177}$Lu composition into the mammalian body.

In certain preferred embodiments, the site will be an infection, tumor, heart, lung, brain, liver, spleen, pancreas, intestine or any other organ. The tumor or infection may be located anywhere within the mammalian body but will generally be in the breast, ovary, prostate, endometrium, lung, brain, colon or liver. The site may also be a folate-positive cancer or estrogen-positive cancer.

The invention also provides a kit for preparing a radiopharmaceutical preparation. The kit generally includes a sealed vial or bag, or any other kind of appropriate container, containing a predetermined quantity of TA2S or DO2S derivative-tissue specific ligand conjugate composition to label the conjugate with the desired radionuclide. In certain cases, the macrocycle-tissue specific ligand conjugate composition will also include a linker between the macrocycle and the tissue specific ligand. The tissue specific ligand may be any ligand that specifically binds to any specific tissue type, such as those discussed herein. When a linker is included in the composition, it may be any linker as described herein.

The components of the kit may be in any appropriate form, such as in liquid, frozen or dry form. In a preferred embodiment, the kit components are provided in lyophilized form. The kit may also include an antioxidant and/or a transchelator. The antioxidant may be any known antioxidant but is preferably vitamin C. Transchelators may also be present to bind unreacted radionuclide. Most commercially-available kits contain glucoheptonate as the transchelator. However, glucoheptonate does not completely react with typical kit components, leaving approximately 10-15% of unused material. This remaining glucoheptonate will go to a tumor and skew imaging results. Therefore, the inventors prefer to use DTPA, EDTA or DOTA as the transchelator as they are cheaper and react more completely.

Another aspect of the invention is a prognostic method for determining the potential usefulness of a candidate compound for treatment of specific tumors. Currently, most tumors are treated with the "usual drug of choice" in chemotherapy without any indication whether the drug is actually effective against that particular tumor until months, and many thousands of dollars, later. The imaging compositions of the invention are useful in delivering a particular drug to the site of the tumor in the form of a labeled macrocycle-drug conjugate and then imaging the site within hours to determine whether a particular drug is taken up and retained.

In that regard, the prognostic method of the invention includes the steps of determining the site of a tumor with a macrocycle which is conjugated to a tumor specific cancer chemotherapy drug candidate, administering the composition to the mammalian body and imaging the site to determine the effectiveness of the candidate drug against the tumor. Typically, the imaging step will be performed within about 10 minutes to about 4 hours after injection of the composition into the mammalian body. Preferably, the imaging step will be performed within about 1 hour after injection of the composition into the mammalian body.

The cancer chemotherapy drug candidate to be conjugated to macrocycles in the prognostic compositions may be chosen from known or yet to be developed cancer chemotherapy drugs. Such drugs are known to those of ordinary skill in the art. There are many anticancer agents known to be specific for certain types of cancers. However, not every anticancer agent for a specific type of cancer is effective in every patient. Therefore, the present invention provides a method of determining possible effectiveness of a candidate drug before expending a lot of time and money on treatment.

Yet another embodiment of the present invention is a reagent for preparing a scintigraphic imaging agent. The reagent of the invention includes a tissue specific ligand, having an affinity for targeted sites in vivo sufficient to produce a scintigraphically-detectable image, covalently linked to a radionuclide binding moiety. The radionuclide binding moiety is either directly attached to the tissue specific ligand or is attached to the ligand through a linker as described above. The radionuclide binding moiety is preferably a tetraaza compound. For example, the tissue specific ligand may be covalently linked to one or both acid arms of the TA2S derivative or DO2S derivative, either directly or through a linker and/or one or both of the secondary amines, either directly or through a linker as described above. The tissue specific ligand may be any of the ligands as described above.

Suitable bifunctional chelators generally serve two main purposes: 1) to coordinate the radiometal and 2) to provide a molecular backbone that can be modified with functional groups for attachment to the targeting molecule. Conjugation of radiometal chelators can be applied to multiple classes of compounds described below. In certain embodiments these subsequent bioconjugates could then be radiolabeled using the apparatus of the present invention through an automated synthetic scheme to yield the final form of the radiotracer.

II. Targeting Ligands

TA2S derivatives or DO2S derivatives may be used to target tumors (e.g., cancerous, precancerous, benign), tumor angiogenesis, hypoxia, apoptosis defects, disease receptors (e.g., cell receptors that are indicative of cancer), disease functional pathways (e.g., a metabolic pathway that has been altered by a disease state), and disease cell cycles. Additionally, TA2S derivatives or DO2S derivatives may be used for the assessment of a pharmaceutical agent's effectiveness on these biochemical processes.

TA2S derivatives or DO2S derivatives may also be used as a diagnostic tool and/or for predicting responses to certain kinds of treatment. For example, conjugates of TA2S derivatives or DO2S derivatives and tamoxifen (an estrogen receptor targeting ligand) may be used to image cancerous tumors; in this example, the imaging may provide important information about the disease such as to what degree the cancerous cells express the estrogen receptor which can be used to predict how the disease will respond to treatments that target cells expressing the estrogen receptor (e.g., when it is identified that cancerous tumors selectively express high levels of estrogen receptor, this information indicates that the cancerous cells will likely respond to therapeutic doses of anti-cancer agents that target cells expressing the estrogen receptor). This approach is referred to as "image guided therapy".

An advantage of conjugating a TA2S derivative or DO2S derivative with a tissue targeting ligands is that the specific binding properties of the tissue targeting ligand can concentrate the radioactive signal over the area of interest. It is envisioned that the derivatives used for imaging and/or therapy may comprise a TA2S derivative or DO2S derivative conjugated to a targeting ligand designed for targeting cancerous tumors, pre-cancerous tumors, disease receptors, hypoxic tissues (hypoxia), apoptosis pathways, disease cell cycles, and/or disease functional pathways. The TA2S derivatives or DO2S derivatives may also be used for assessing a pharmaceutical agent's effectiveness on various metabolic and/or biochemical pathways or individual reactions. Examples of certain targeting ligands which may be used the present invention can be found in Table 1. In certain embodiments, an anti-cancer drug may be used as a targeting ligand. Anti-cancer drugs are well known in the art (e.g., Connors, 1996). For example, a table from U.S. Pat. No. 6,692,724 lists several examples of anti-cancer drugs which may be used as targeting ligands in various embodiments of the present invention. U.S. Pat. No. 6,692,724 is incorporated by reference as though fully disclosed herein.

TABLE 1

| Targets for DO2S Derivatives | Examples of Targeting Ligands |
|---|---|
| Tumor Angiogenesis | Celecoxib, C225, angiostatin |
| Disease Receptor | tamoxifen, α-β tyrosine, tyrosine, alpha methyltyrosine, luteinizing hormone, transferrin, somatostatin, androgen, estrogen, estrone, progesterone, tetraacetate mannose, |

TABLE 1-continued

| Targets for DO2S Derivatives | Examples of Targeting Ligands |
|---|---|
| Disease Cell Cycle | adenosine, penciclovir |
| Pharmaceutical Agent Assessment | carnitine, puromycin |
| Apoptosis Targeting | TRAIL monoclonal antibody, caspase-3 substrate, Bcl family member |

Classes of Targeting Molecules

In the present invention, it is generally preferable to conjugate a targeting moiety (e.g., an anticancer drug) to the TA2S derivative or DO2S derivative; however, in certain embodiments a TA2S or DO2S derivative that is not conjugated to a targeting moiety may be used for imaging and therapy. A targeting moiety may be conjugated to the TA2S or DO2S derivative via several methods. One method is to synthesize a halide (e.g., iodinated) targeting moiety. For example, the hydroxy group of a targeting moiety (e.g., a hydrophobic molecule) may be converted to a tosyl-, mesyl-, triflate or halide (e.g., iodine) group. In certain embodiments of the present invention, the final product is soluble in water after hydrochloride or sodium salt formation. Alternatively, another method to conjugate DO2S compound to a targeting moiety is to synthesize a sulfonate (e.g., tosyl-mesyl or triflate) targeting moiety. Di-, tri- or all substitutes on the DO2S derivative may be prepared by reacting these iodinated or sulfonate targeting agents. For mono-substitutes on the carbonyl group, a selective protection of nitrogen groups is needed. Targeting ligands that may be conjugated with a TA2S or DO2S derivative include amino acids (e.g., tyrosine, serine), amino acid derivatives (e.g., alphamethyltyrosine), glucosamine, estrone, and tetraacetate mannose.

Other ligands may also be conjugated to the TA2S or DO2S derivative. In general, the ligands for use in conjunction with the present invention will possess either a halide or a hydroxy group that are able to react with and covalently bind to the TA2S or DO2S derivative on either one or both acid arms and/or on one or both amino arms. Ligands contemplated for use in the present invention include, but are not limited to, angiogenesis/antiangiogenesis ligands, DNA topoisomerase inhibitors, glycolysis markers, antimetabolite ligands, apoptosis/hypoxia ligands, DNA intercalators, receptor markers, peptides, nucleotides, antimicrobials such as antibiotics or antifungals, organ specific ligands and sugars, and agents that mimic glucose.

It is contemplated that virtually any targeting ligand that is known, or may be subsequently discovered, that possesses a hydroxy group or a halide, or alternatively may have a hydroxy group or halide introduced into its structure (e.g., via the addition of a sidechain, or by attaching a halide to a phenol group in the targeting ligand), may be used with the present invention. In certain embodiments, a targeting ligand may be directly conjugated to a TA2S or DO2S derivative, or a targeting ligand may be indirectly conjugated to a TA2S or DO2S derivative via a linker. It is envisioned that targeting ligands that have previously been conjugated to another (non-TA2S or DO2S compound) chelator, such as diaminodithiol chelators, may be conjugated to TA2S or DO2S derivative of the present invention and used for therapeutic purposes; in certain instances, it may be required to modify the targeting ligand (e.g., adding a side chain that contains a hydroxyl or a halide) in order to covalently bind the targeting ligand to the TA2S or DO2S derivative.

Classes of targeting molecules include, but are not limited to, disease cell cycle targeting compounds, angiogenesis targeting ligands, tumor apoptosis targeting ligands, disease receptor targeting ligands, drug-based ligands, antimicrobials, agents that mimic glucose, tumor hypoxia targeting ligands, extracellular matrix targeted ligands and the like.

1. Cellular Proliferation

Disease cell cycle targeting refers to the targeting of agents that are upregulated in proliferating cells. Compounds used for this purpose are also known as proliferation targeteing ligands and can be used to measure various parameters in cells, such as tumor cell DNA content. Certain disease cell cycle targeting ligands are nucleoside analogues. For example, pyrimidine nucleosides (e.g., 2'-fluoro-2'-deoxy-5-iodo-1-β-D-arabinofuranosyluracil (FIAU), 2'-fluoro-2'-deoxy-5-iodo-1-β-D-ribofuranosyl-uracil (FIRU), 2'-fluoro-2'-5-methyl-1-β-D-arabinofurano-syluracil (FMAU), 2'-fluoro-2'-deoxy-5-iodovinyl-1-β-D-ribofuranosyluracil (IVFRU) and acycloguanosine: 9-[(2-hydroxy-1-(hydroxymethyl)ethoxy)methyl]guanine (GCV) and 9-[4-hydroxy-3-(hydroxy-methyl)butyl]guanine (PCV) (Tjuvajev et al., 2002; Gambhir et al., 1998; Gambhir et al., 1999) and other 18F-labeled acycloguanosine analogs, such as 8-fluoro-9-[(2-hydroxy-1-(hydroxymethyl)ethoxy)methyl]guanine (FGCV) (Gambhir et al., 1999; Namavari et al., 2000), 8-fluoro-9-[4-hydroxy-3-(hydroxymethyl)butyl]guanine (FPCV) (Gambhir et al., 2000; Iyer et al., 2001), 9-[3-fluoro-1-hydroxy-2-propoxy methyl]guanine (FHPG) (Alauddin et al., 1996; Alauddin et al., 1999), and 9-[4-fluoro-3-(hydroxymethyl)butyl]guanine (FHBG) (Alauddin and Conti, 1998; Yaghoubi et al., 2001) have been developed as reporter substrates for imaging wild-type and mutant (Gambhir et al., 2000) HSV1-tk expression. Any combination of the foregoing are useful in the practice of the invention. One or ordinary skill in the art would be familiar with these and other agents that are used for disease cell cycle targeting.

2. Angiogenesis Targeting

Throughout this application, "tumor angiogenesis targeting" refers to the use of an agent to bind to tumor neovascularization and tumor cells. Agents that are used for this purpose are known to those of ordinary skill in the art for use in performing various tumor measurements, including measurement of the size of a tumor vascular bed, and measurement of tumor volume. Some of these agents bind to the vascular wall. One of ordinary skill in the art would be familiar with the agents that are available for use for this purpose. A tumor angiogenesis targeting ligand is a ligand that is used for the purpose of tumor angiogenesis targeting as defined above. Examples of angiogenesis targeting ligands include COX-2 inhibitors, anti-EGF receptor ligands, herceptin, angiostatin, C225, VEGF, RGD peptides, $\alpha_v\beta_3$ NGR peptides, and thalidomide. COX-2 inhibitors include, for example, celecoxib, rofecoxib, etoricoxib, and analogs of these agents. Any combination of the foregoing are useful in the practice of the invention.

3. Tumor Apoptosis Targeting

"Tumor apoptosis targeting" refers to the use of an agent to bind to a cell that is undergoing apoptosis or is at risk of undergoing apoptosis. These agents are generally used to provide an indicator of the extent or risk of apoptosis, or programmed cell death, in a population of cells, such as a tumor. Significant research is directed towards the creation and evaluation of new compounds that affect apoptosis, such as restoring apoptosis sensitivity to cancer cells (Reed, 2003). It is envisioned that the present invention may be used to expedite the evaluation and/or efficacy of known and/or subsequently discovered tumor apoptosis targeting compounds. One of ordinary skill in the art would be familiar with agents that are used for this purpose. Certain examples of apoptosis targeting agents are shown in Table 1. A "tumor apoptosis targeting ligand" is a ligand that is capable of performing "tumor apoptosis targeting" as defined in this paragraph. Examples of tumor apoptosis ligands include a TRAIL (TNF-related apoptosis inducing ligand) monoclonal antibody. TRAIL is a member of the tumor necrosis factor ligand family that rapidly induces apoptosis in a variety of transformed cell lines. Other examples of tumor apoptosis targeting ligands include a substrate of caspase-3, such as peptide or polypeptide that includes the 4 amino acid sequence aspartic acid-glutamic acid-valine-aspartic acid, and any members of the Bcl, PRELI-MSF-1 and Apoptosis Inducing Factor (AIF) families.

4. Disease Receptor Targeting

In "disease receptor targeting," certain agents are exploited for their ability to bind to certain cellular receptors that are overexpressed in disease states, such as cancer. Examples of such receptors which are targeted include estrogen receptors, amino acid transporters, androgen receptors, pituitary receptors, transferrin receptors, progesterone receptors, ABC family drug transporters, chemokine receptors, cytokine receptors, hormone receptors, stem cell markers and glucose transporters. Examples of agents that can be applied in disease-receptor targeting are shown in Table 1. Disease receptor targeting ligands (e.g., pentetreotide, octreotide, transferrin, and pituitary peptide) bind to cell receptors, some of which are overexpressed on certain cells. The folate receptor is included herein as another example of a disease receptor.

Estrogen, estrone, and tamoxifen target the estrogen receptor. Estrogen receptors are over expressed in certain kinds of cancer, and DO2S derivatives that comprise an estrogen receptor targeting ligand may be used in certain embodiments to image tumors. The expression of estrogen receptors is also altered in the diseases of osteoporosis and endometriosis. It is anticipated that a DO2S derivative comprising an estrogen receptor targeting ligand may be used to image other diseases such as osteoporosis and endometriosis.

Glucose transporters are overexpressed in various diseased cells such as certain cancerous cells. Tetraacetate mannose, deoxyglucose, certain polysaccharides (e.g., neomycin, kanamycin, tobramycin), and monosaccharides (e.g., glucosamine) also bind the glucose transporter and may be used as disease receptor targeting ligands. Since these ligands are not immunogenic and are cleared quickly from the plasma, receptor imaging would seem to be more promising compared to antibody imaging.

Similarly, amino acid transporters are also overexpressed in various diseased cells such as certain cancerous cells. Amino acids and/or amino acid derivatives (e.g., serine, tyrosine, alpha methyltyrosine) may be used as disease receptor targeting ligands.

The ATP-binding cassette (ABC) family of transporters are overexpressed in tumors and have been shown to regulate multidrug resistance. Members of this family include MRP-1, p-glycoprotein, LRP, BCRP, CFTR OABP and the GNC20 family. Examples of ABC family substrates which could be conjugated to DO2S compounds include verapamil, quinidine, diltiazen, ritonavir, docetaxel, topoisomerase inhibitors, 2-methoxy isobutyl isonitrile (MIBI) and cyclosporine A.

Additional receptor targeting ligands are available and may be conjugated to DO2S compounds. Stem cell and progenitor cell surface markers are overexpressed in tumors. Ligands which bind to these receptors include members of the notch, WNT, tumor growth factor (TGF), cadherin, desmoglien, and hedgehog families, alphafetoprotein, shyaluronic acid, erythropoietin, stem cell factor (SCF), as well as ligands to CD34, CD-44, c-kit, Sca-1 and CD133. Other examples of disease receptor targeting ligands include leuteinizing hormone and transferrin. Folic acid, folate, tomudex, and methotrexate are examples of disease receptor targeting ligands that bind folate receptors.

"Tumor targeting" refers to the ability of a compound to preferentially associate with tumors (e.g., cancerous, precancerous, and/or benign). A "tumor targeting ligand" refers to a compound which preferentially binds to or associates with tumor tissues, as compared to non-tumor tissues. Ligands (e.g., small molecules or antibodies) which preferentially target tumors are well known in the art, and it is anticipated that tumor targeting ligands that are currently known, or which may be subsequently discovered, may be used with the present invention.

5. Drug-based Ligands

Certain drug-based ligands can be applied in measuring the pharmacological response of a subject to a drug. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject. Examples of drug-based ligands include carnitine and puromycin.

6. Microbial Agents

Any antimicrobial is contemplated for inclusion as a targeting ligand. Preferred antimicrobials include ampicillin, amoxicillin, penicillin, cephalosporin, clidamycin, gentamycin, kanamycin, neomycin, natamycin, nafcillin, rifampin, tetracyclin, vancomycin, bleomycin, and doxycyclin for gram positive and negative bacteria and amphotericin B, amantadine, nystatin, ketoconazole, polymycin, acyclovir, and ganciclovir for fungi.

7. Agents that Mimic Glucose

Agents that mimic glucose (glucose-mimicking agents) are also contemplated for inclusion as targeting ligands. Preferred agents that mimic glucose, or sugars, include neomycin, kanamycin, gentamycin, paromycin, amikacin, tobramycin, netilmicin, ribostamycin, sisomicin, micromicin, lividomycin, dibekacin, isepamicin, astromicin, aminoglycosides, glucose or glucosamine.

Disease cell glycolysis targeting refers to the targeting of agents that are upregulated in glucose utilization in cells. Compounds used for this purpose can be used to measure various parameters in cells, such as tumor cell growth, inflammation degrees. Certain disease cell glycolysis targeting ligands are glucose, galactose, mannose and ribose analogues.

8. Hypoxia Targeting

In certain embodiments, a tumor targeting ligand may associate with tumor tissues by targeting the hypoxia associated with tumor cells. Examples of tumor targeting ligands that target hypoxic tissues (hypoxia targeting agents) include nitroimidazole and metronidazole, and these ligands may also be used to target other hypoxic tissues that are hypoxic due to a reason other than cancer (e.g., stroke).

Tumor hypoxia targeting ligands are also useful in certain embodiments of the present invention. Misonidazole, an example of a tumor hypoxia targeting ligand, is a hypoxic cell sensitizer, and labeling MISO with different radioisotopes (e.g., $^{68}$Ga, $^{99m}$Tc, $^{111}$In) may be useful for differentiating a hypoxic but metabolically active tumor from a well oxygenated active tumor by PET or planar scintigraphy. [$^{18}$F]Fluoromisonidazole (FMISO) has been used with PET to evaluate tumor hypoxia.

Disease cell hypoxia targeting refers to the targeting of agents that are upregulated in hypoxia cells. Compounds used for this purpose can be used to measure various parameters in cells, such as tumor cell hypoxia, resistance or residual content.

9. Extracellular Matrix and Lipid Raft Targeted Ligands

Extracellular matrix (ECM) proteins have been implicated in multiple disease states including inflammation, atherosclerosis, and tumorogenesis. Examples of ECM targeted ligands include agrin, thrompospondin, and members of the collagen, matrilin and laminin families. Fibronectin and endostatin are also examples of ECM targeted ligands. Plasma membrane lipids are involved in compartmentalizing signal transduction events initiated by cell adhesion to the extracellular matrix. Examples of lipid raft-associated targets include ligands which bind integrins, cholesterol, sphigolipids, glycosylphosphatidylinositol (GPI)-anchored proteins and Rho and Rac family GTPases.

III. Formulation of TA2S and DO2S Derivatives

To quench the radiolabeling reaction, a transchelator can be added to the radioactive solution to chelate any unbound radioisotope. Examples of acceptable transchelators for radionuclides include polycarboxylic acids, e.g., tartrate, citrate, phthalate, iminodiacetate, DOTA, EDTA, DTPA and the like. Additionally, any of a variety of anionic and/or hydroxylic oxygen-containing species could serve this function, e.g., salicylates, acetylacetonates, hydroxyacids, catechols, glycols and other polyols, e.g., glucoheptonate, and the like. Other suitable reagents and protocols for the formulation of radiopharmacueticals will be apparent to those skilled in the art and may be readily adapted for use with the apparatus of the present invention.

IV. LINKERS

If amino or hydroxy groups are not available (e.g., acid functional group), a desired ligand may still be conjugated to the TA2S or DO2S derivative using the methods of the invention by adding a linker, such as ethylenediamine, amino propanol, diethylenetriamine, aspartic acid, polyaspartic acid, glutamic acid, polyglutamic acid, lysine, poly(ethylene) glycols or any combination thereof. For example, U.S. Pat. No. 6,737,247 discloses several linkers which may be used with the present invention and is hereby incorporated by reference in its entirety without disclaimer. U.S. Pat. No. 5,605,672 discloses several "preferred backbones" which may be used as linkers in the present invention and is hereby incorporated by reference in its entirety. In certain embodiments, a TA2S or DO2S compound may be conjugated to a linker, and the linker is conjugated to the targeting ligand. In other embodiments more than one linker may be used; for example, a TA2S or DO2S derivative may be conjugated to a linker, and the linker is conjugated to a second linker, wherein the second linker is conjugated to the targeting ligand. In, certain embodiments, two, three, four, or more linkers that are conjugated together may be used to conjugate a TA2S or DO2S derivative and targeting ligand. However, it is generally preferable to only use a single linker to conjugate a TA2S or DO2S derivative and a targeting ligand.

V. Conjugates

The term "tetraaza compound conjugate" is defined herein as an tetraaza compound that has been conjugated to at least one other molecule or atom. In certain embodiments the tetraaza compound conjugate comprises a tetraaza compound that has an atom chelated to it. The tetraaza compound conjugate may comprise a tetraaza compound that is conjugated to a targeting ligand (via a covalent bond) and/or a linker (via a covalent bond) and/or a metal chelate (via a coordination bond). The term "TA2S conjugate" is defined herein as an TA2S derivative that has been conjugated to at least one other molecule or atom. In certain embodiments the TA2S conjugate comprises a TA2S derivative that has an atom chelated to it. The TA2S conjugate may comprise a tetraaza compound that is conjugated to a targeting ligand and/or a linker and/or a metal chelate (via a coordination bond). The term "DO2S conjugate" is defined herein as a DO2S derivative that has been conjugated to at least one other molecule or atom. In certain embodiments the DO2S conjugate comprises a DO2S derivative that has an atom chelated to it. The DO2S conjugate may comprise a tetraaza compound that is conjugated to a targeting ligand and/or a linker and/or a metal chelate (via a coordination bond).

In this way, the derivatives may have a metal atom chelated to them (i.e., the conjugate may be labeled with a radioisotope). The metal atom may be radioactive or non-radioactive.

VI. Radioisotope Labeling

To facilitate certain embodiments involving, for example, imaging or the use of a TA2S or DO2A derivative as a therapeutic, a radioisotope may be chelated to the TA2S or DO2A derivative. For example, a DO2A derivative may be labeled with $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi or $^{225}$Ac.

Generally, it is believed that virtually any α-emitter, β-emitter, γ-emitter, or β/γ-emitter can be used in conjunction with the invention. Preferred α-emitters include $^{211}$At, $^{212}$Bi and $^{223}$Ra. Preferred β-emitters include $^{90}$Y and $^{225}$Ac. Preferred β/γ-emitters include $^{67}$Cu, $^{89}$Sr, $^{153}$Sm, $^{166}$Ho, $^{177}$Lu, $^{186}$Re and $^{188}$Re. Preferred γ-emitters include $^{62}$Cu, $^{64}$Cu, $^{67}$Ga, $^{68}$Ga, $^{94m}$Tc, $^{99m}$Tc and $^{111}$In. It is also envisioned that para-magnetic substances, such as Gd, Mn, Cu or Fe can be chelated with DO2S derivatives for use in conjunction with the present invention.

In nuclear imaging, the radiolabel is typically a γ radiation emitting radionuclide and the radiotracer is typically visualized using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A variety of radioisotopes are known to be useful for nuclear imaging and radionuclide therapy, including $^{67}$Ga, $^{68}$Ga, $^{94m}$Tc, $^{99m}$Tc, $^{111}$In, $^{123}$I, $^{125}$I, $^{169}$Yb, $^{177}$Lu, $^{186}$Re and $^{188}$Re. Due to better imaging characteristics and cost-effectiveness, attempts have been made to replace or provide an alternative to $^{111}$In-labeled compounds with corresponding $^{68}$Ga labeled compounds when possible. Due to favorable physical characteristics as well as availability from a generator, $^{68}$Ga is preferred for the labeling of diagnostic radiopharmaceuticals.

Numerous types of generator systems are known to those skilled in the art and any generator system that produces a sufficient quantity of a daughter nuclide can be useful in medical imaging including, but not limited to: $^{44}$Ti/$^{44}$Sc, $^{52}$Fe/$^{52m}$Mn, $^{62}$Zn/$^{62}$Cu, $^{68}$Ge/$^{68}$Ga, $^{72}$Se/$^{72}$As, $^{82}$Sr/$^{82}$Rb, $^{99}$Mo/$^{99m}$Tc, $^{118}$Te/$^{118}$Sb, $^{122}$Xe/$^{122}$I, $^{128}$Ba/$^{128}$Cs, $^{178}$W/$^{178}$Ta, $^{188}$W/$^{188}$Re, $^{195m}$Hg/$^{195m}$Au.

A number of factors must be considered for optimal radioimaging in humans. In certain embodiments, the TA2S or DO2A derivative may be labeled with $^{68}$Ga for PET imaging or $^{177}$Lu (a β and γ-emitter) for systemic radionuclide therapy. When chelated with non-radioactive metals (e.g. copper, cobalt, platinum, iron, arsenic, rhenium, germanium), the cold (non-radioactive) TA2S or DO2A derivative may be used as a metallic chemotherapeutic agent. One aspect of the uniqueness of this technology is to use existing PET sulfonate precursors or SPECT iodinated agents to react with a DO2A compound and produce a chelator-based analogue of such agents. The end product may then be used to chelate metals, which have less complex chemistries and are more accessible and affordable than non-metallic radionuclides.

Gallium-68 is positron-emitting radioisotope produced from a $^{68}$Ge/$^{68}$Ga generator ($t_{1/2}$=271 days). Commercially-available $^{68}$Ge/$^{68}$Ga generators use diluted forms of hydrochloric acid for elution. The eluate is collected in large volumes and is not in a suitable form for radiolabeling of pH sensitive materials or amenable to typical in vitro and in vivo studies. Therefore, removal of HCl is desired and can been achieved through evaporation or ion-exchange methods yielding a concentrated solution of $^{68}$Ga. The resulting $^{68}$Ga$^{3+}$ cation can form stable complexes with many ligands containing oxygen, nitrogen and sulfur as donor atoms, making it suitable for complexation with a wide range of chelators and macromolecules. For certain embodiments of the present invention involving chelating $^{68}$Ga to TA2S or DO2S derivative or to a TA2S or DO2S conjugate, it is typically preferable that $^{68}$Ga be in aqueous buffer solutions, most preferably in sodium acetate buffer. These solutions provide an ideal environment for forming the chelate with TA2S or DO2S derivative or a TA2S or DO2S conjugate. It is known to those having skill in the art that various buffers can also be used during $^{68}$Ga chelation.

Therapeutic radionuclides emit radiation which interacts with tissues and cellular components typically resulting in cellular damage. Virtually any α-emitter, β-emitter, or auger electron-emitter can exert a therapeutic effect on its target. Pure β-emitters have longer pathlengths in tissue and are preferred for larger tumors, however they lack imaging capabilities and utilize a diagnostic surrogate to provide biodistribution and dosimetry information. Certain radionuclides possess both β and γ-emissions allowing for a diagnostic scan of the agent using low radioactive doses, followed by increasing radioactive doses to treat the site of interest. $^{177}$Lu is an example of a β/γ-emitting radionuclide which can be used with this invention to prepare a targeted agent with diagnostic and therapeutic characteristics. Other examples of β/γ-emitters include $^{89}$Sr, $^{153}$Sm, $^{166}$Ho, $^{186}$Re and $^{188}$Re. Due to favorable decay characteristics such as half-life (6.73 days), beta emission (490 keV) and gamma emission (113 keV [6.4%], 208 keV [11%]) for imaging, $^{177}$Lu is preferred for the labeling of therapeutic radionuclides.

In addition to imaging tumors with TA2S or DO2S derivatives labeled with radionuclides, it is envisioned that these compounds may also be used for imaging of tissue related to other diseases, as well as diagnostics related to cancer and other diseases. For example, it is contemplated that the TA2S or DO2S derivatives labeled with radionuclides of the invention may be useful to image not only tumors, but also other tissue-specific conditions, such as infection, hypoxic tissue (stroke), myocardial infarction, apoptotic cells, Alzheimer's disease and endometriosis. An advantage of imaging using a TA2S or DO2S derivative that comprises a radiolabeled TA2S or DO2S derivative that is conjugated to a tissue targeting ligand is that the specific binding properties of the tissue targeting ligand concentrates the radioactive signal over the area of interest.

VII. Kit for Preparing Radiolabeled DO2S Conjugates

Complexes and means for preparing such complexes may be provided in a kit form that typically includes a sealed vial containing a predetermined quantity of a TA2S or DO2S conjugate of the invention to be labeled with a radionuclide. In some embodiments of the present invention, the kit includes a radionuclide. In certain further embodiments, the radionuclide is $^{e}$Ga or $^{177}$Lu. The kit may also contain conventional pharmaceutical adjunct materials such as, for example, pharmaceutically acceptable salts to adjust the osmotic pressure, buffers, preservatives, antioxidants, and the like. Reducing agents may also be included in kits when the radioisotope is $^{99m}$Tc or $^{188}$Re.

In certain embodiments, an antioxidant and a transchelator are included in the composition to prevent oxidation of the TA2S or DO2S conjugate. In certain embodiments, the antioxidant is vitamin C (ascorbic acid). However, it is contemplated that any other antioxidant known to those of ordinary skill in the art, such as gentisic acid, tocopherol, pyridoxine, thiamine, or rutin, may also be used. Examples of transchelators for use in the present invention include, but are not limited to, glucoheptonate, gluconate, glucarate, citrate, and tartarate. The components of the kit may be in liquid, frozen or dry form. In certain embodiments, kit components may be provided in lyophilized form.

VIII. Uses for DO2S Conjugates

The TA2S or DO2S conjugates of the invention may also be used for prognostic purposes. It is envisioned that TA2S or DO2S conjugates may be administered to a patient having a tumor. It is envisioned that the use of a radiolabeled TA2S or DO2S conjugates as a labeling strategy can be effective using ligands designed for targeting disease receptors, hypoxia markers, apoptosis defects, disease cell cycles, disease functional pathways, and assessment of pharmaceutical agents effectiveness of these biochemical processes. Imaging may be performed to determine the effectiveness of the TA2S or DO2S conjugate against a patient's specific problem relating to disease receptors, hypoxia markers, apoptosis defects, disease cell cycles, disease functional pathways, and assessment of pharmaceutical agent's effectiveness on these biochemical processes. Using this methodology, physicians can quickly determine which TA2S or DO2S conjugate will be most effective for the patient and design the corresponding therapy or mode of treatment. This methodology possesses significant advantages over methods involving first choosing a drug and administering a cycle of chemotherapy, which may involve months of the patient's time at a substantial physical and financial cost before the effectiveness of the cancer chemotherapeutic agent can be determined.

The present invention may also be used to monitor the progress of former patients who have successfully undergone chemotherapy or radiation treatment to determine if cancer has remained in remission or is metastasizing. People with a history of cancer in their family or who have been diagnosed with a gene(s) associated with cancer may undergo monitoring by health professionals using the methodology of the current invention. The methods and pharmaceutical agents of the current invention may also be used by a health professional to monitor if cancer has started to develop in a person with cancer risk factors, such as environmental exposure to carcinogens. Such methods to monitor the progress and/or recurrence of cancer and other diseases, known to those of skill in the art, are all applicable to the present invention and that the present invention may be used in such methods should be understood.

The present invention may also be used for the delivery of radionuclide therapy. A therapeutic radionuclide may be chelated by a TA2S or DO2S conjugate and used for targeted treatment of disease. For example, $^{177}$Lu has a beta emission of 498 keV which is suitable for therapy, and it also possesses a gamma emission which can allow for accurate dosimetry and imaging of $^{177}$Lu-conjugates. The ability to directly image and assess the biodistribution and dosimetry of therapeutic radionuclides in vivo will assist in determining target specificity as well as validating the localization of dose over time. Chelation of $^{177}$Lu to a TA2S or DO2S conjugate would allow targeting of the radionuclide complex to tumor cells and spare non-target organs from unnecessary radiation dose. Other variations, known to those having skill in the art upon a reading of this disclosure are included in the present invention.

The present invention includes embodiments that are useful for the targeted delivery of metallic therapy. Toxic metals can be chelated to TA2S or DO2S conjugates and used for the treatment of cancer. Metals of interest include but are not limited to gallium, iron, arsenic and platinum. For example, DO2S-derivative 1 conjugated to folic acid could also chelate platinum for folate receptor-targeted therapy in folate receptor-positive cancers. It is envisioned that such an approach would increase specificity of drug delivery with reduced systemic toxicity which is typically associated with non-targeted delivery of such metals. A radiotracer using the radioactive form of the respective metal could be developed and serve as a guide for biodistribution, selection of response in different tumor types and pharmacokinetic characterization. This and related embodiments of the present invention will be known to those having skill in the art upon a reading of the present specification.

IX. Drug Assessment

Certain drug-based ligands of the present invention can be applied in measuring the pharmacological response of a subject to a drug. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject. Radiolabeled agents can be applied in measuring drug assessment.

X. Pharmaceutical Preparations

Pharmaceutical compositions of the present invention comprise an effective amount of a DO2S derivative of the present invention dissolved or dispersed in a pharmaceutically acceptable carrier. The phrases "pharmaceutical" or "pharmacologically acceptable" refer to molecular entities and compositions that do not produce an adverse, allergic or other untoward reaction when administered to an animal, such as, for example, a human, as appropriate. The preparation of a pharmaceutical composition that contains at least one TA2S or DO2S derivative, such as a radiolabeled TA2S or DO2S derivative, or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The DO2S derivatives of the present invention may comprise different types of carriers depending on whether it is to be administered in solid, liquid or aerosol form, and whether it needs to be sterile for such routes of administration such as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a TA2S or DO2S derivative. In other embodiments, the active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The TA2S or DO2S derivative may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof such methods. In many cases, it will be preferable to include isotonic agents, such as, for example, sugars, sodium chloride or combinations thereof.

Sterile injectable solutions are prepared by incorporating the TA2S or DO2S derivative in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

XI. Combinational Therapy

It is an aspect of this invention that TA2S or DO2S derivatives, such as a radiolabeled TA2S or DO2S derivative, of the present invention can be used in combination with another agent or therapy method, preferably another cancer treatment. The TA2S or DO2S derivative may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the TA2S or DO2S derivative. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the DO2S derivative. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the TA2S or DO2S derivative. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, the DO2S derivative is "A" and the secondary agent, which can be any other therapeutic agent, is "B":

A/B/A B/A/B B/B/A A/A/B A/B/B B/A/A A/B/B/B B/A/B/B

B/B/B/A B/B/A/B A/A/B/B A/B/B/A A/B/B/A B/B/A/A

B/A/B/A B/A/A/B A/A/A/B B/A/A/A A/B/A/A A/A/B/A

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the TA2S or DO2S derivative. These therapies include but are not limited to chemotherapy, radiotherapy, immunotherapy, gene therapy and surgery.

a. Chemotherapy

Cancer therapies also include a variety of combination therapies with both chemical and radiation based treatments. Combination chemotherapy include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, COX-2 inhibitors, cholesterol synthesis inhibitors, cisplatinum, 5-fluorouracil, vincristin, vinblastin, methylxanthine derivatives, wortmanin, rapamycin, forskolin, staurosporine, streptozocin, fludurabine, methotrexate, genistein, curcumin, resveratrol, silymarin, caffeic acid phenethyl ester, flavopiridol, emodin, green tea polyphenols, piperine, oleandrin, ursolic acid, butamic acid, actinomycin D, thalidomide or any analog or derivative variant of the foregoing.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Radiochemotherapy

Radiochemotherapy is the combined delivery of radiation and chemotherapy to a target. This can be achieved in a single agent through conjugation of a chemotherapeutic agent to a chelating moiety which is then subsequently radiolabeled with a therapeutic radionuclide. Combinations of radiochemotherapy include, for example, cisplatin (CDDP) with α-emitters, cyclophosphamide with β-emitters, doxorubicin with β/γ-emitters and taxol with Auger-emitters, or any analog or derivative variant of the foregoing.

d. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody may also be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy could thus be used as part of a combined therapy, possibly in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

e. Gene Therapy

In yet another embodiment, the secondary treatment is a secondary gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues.

f. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically or partially removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

XII. Synthetic Pathways

EXAMPLE 1

Synthesis of DO2A-glucosamine

The N4 compound starting materials for the tetraaza compounds are commercially available. Examples of how one would make the novel modifications of these macrocyclic compounds for the present invention herein are provided below.

This example illustrates the synthesis of DO2A-(Glucosamine)$_2$. DO2A-tert-butyl ester (1,4,7,10-Tetraazacyclododecane-1,7-bis(t-butyl acetate) (0.215 g, 0.538 mmoles) was dissolved in 2 mL of trifluoroacetic acid, 0.1 mL of water, and 0.4 mL of methylene chloride. After stirring for 2 h at room temperature, the solvent was evaporated under vacuum. The product was dissolved in 3 mL of methanol and 2 mL of water and extracted twice with 4 mL of methylene chloride. The aqueous layer was concentrated under vacuum to yield DO2A-(COOH)$_2$ as a light yellow oil. Product was dissolved in 1 mL of methanol and left at temperature 4° C. for 2 days yielding colorless crystals.

DO2A-(COOH)$_2$ (0.1748 g, 0.523 mmoles) was dissolved in 1.46 mL of DMSO and 0.122 mL of Et$_3$N, and 0.464 g of BOP (1H-benzotriazol-1-yloxy-tris(dimethylamino)phosphonium hexafluorophosphate) was added. Reaction mixture was stirred for 1 h at room temperature. Glucosamine hydrochloride (0.23 g, 1.046 mmoles) dissolved in 0.2 mL of Et$_3$N and 1.57 mL of DMSO/Et$_2$O (ratio 34:66 v/v) was added to pre-activated solution of DO2A(COOH)$_2$. Reaction mixture was stirred at room temperature for 3 days. After solvent evaporation under vacuum, residue was dissolved in 4 mL of methanol and 1 mL of water and extracted twice with methylene chloride. The aqueous fraction was concentrated under vacuum, redissolved in 0.3 mL of methanol and 1 mL of Et$_2$O, then stored at room temperature for 2-3 days yielding light yellow crystals of product. Product was purified and analyzed by reverse phase RP-HPLC (Phenomenex, C18 column, UV detection at 251 and 280 nm) using binary gradient: 0%-25% buffer B (buffer A: H$_2$0+0.01% TFA, buffer B: CH$_3$CN+ 0.01% TFA), flow rate: 0.3 mL/min.

EXAMPLE 2

Synthesis and Radiolabeling of $^{68}$Ga-(Glucosamine)-$_2$-DO2A-(COOH)$_2$ and $^{68}$Ga-(Glucosamine)-$_3$-DO2A-COOH Conjugates This example illustrates the synthesis and radiolabeling of $^{68}$Ga-(Glucosamine)$_2$-DO2A-(COOH)$_2$ and $^{68}$Ga-(Glucosamine)$_3$-DO2A-COOH conjugates. To a solution of 1,4,7,10-tetraazacyclododecane-1,4,7,10-tetraacetic acid (0.145 g, 0.283 mmoles) dissolved in 0.187 mL of DIPEA (N,N-disopropylethylamine) and 9.76 mL of NMP (N-methyl-pyrrolindone), 0.430 g (1.132 mmoles) of HATU was added. The reaction mixture was stirred for 20 min at room temperature. Glucosamine hydrochloride (1.132 mmoles, 0.244 mg) was dissolved in 6 mL of NMP and 0.187 mL of DIPEA and added to a pre-activated solution of DO2A-(COOH)$_4$. Reaction mixture was stirred at room temperature for 24 h. After solvent evaporation, residue was dissolved in 3 mL water and extracted with methylene chloride. The aqueous layer was evaporated in vacuum yielding yellow oil. Product was precipitated with diethyl ether and analyzed by reverse phase RP-HPLC (Phenomenex, C18, UV detection at 251 and 280 nm using a binary gradient 0%-45% buffer B (buffer A: H$_2$O, buffer B: CH$_3$CN+0.1% TFA) in 20 min, flow rate 2 mL/min. The product was a mixture of the of disubstituted and trisubstituted DO2A-glucosamine conjugates and was purified by RP-HPLC.

20 nmoles of (Glucosamine)$_2$-DO2A-(COOH)$_2$ was dissolved in sodium acetate buffer (pH 4). $^{68}$Ga was eluted from a $^{68}$Ge/$^{68}$Ga generator and buffered to pH 4 using solid sodium acetate. 50 µCi of $^{68}$Ga was added to the conjugate and heated at 95° C. for 10 min. The labeling reaction was monitored using instant-thin-layer-chromatography with a mobile phase of 0.1 M ammonium acetate:methanol (1:1 v/v) and quantified using a radio-TLC scanner (Bioscan). Radiochemical purity was >95%.

FIG. 1 provides synthetic scheme of DO2A-bis(tert-Bu) ester (1a) and synthetic pathways for the ligand attachment to a DO2S derivatives and DO2S derivative-1 (1b). It should be understood that schematic structures of TA2S derivatives and even tetraaza compounds are analogous. FIG. 1c. shows schemes that illustrate the attachment of one or more than one ligand to the DO2S ring. FIG. 1d. shows a table providing illustrative (non-limiting) examples of various ligands and the coupling agents useful in the synthesis.

FIG. 2 illustrates the preparation of mono- and di-aminosugar-containing DO2S derivatives labeled with radiometals. Deprotection of carboxyl groups of DO2A-bis(tert-Bu) ester or its derivatives proceed in the presence of TFA (trifluoroacetic acid). The conjugation reaction of the DO2A-acid to the amino sugar (e.g. glucosamine hydrochloride, galactosamine hydrochloride) is performed by activation of carboxyl group of DO2A by HBTU (O-benzotriazole-,N,N,N', N'-tetramethyluronium-hexafluorophosphate) and HOBT (1-hydroxybenzo-triazole) in the presence of DIEA (N,N-diisopropylethylamine) in DMF. The selectivity of this reaction is controlled by the temperature and stoichiometry of reagents. Method is used to prepare of DO2S-dendrimers and their derivatives modified with polyamino sugar ligands. See Y. Ye, S. Bloch, S. Achilefu, *Journal of the American Chemical Society,* 2004, 126 (25), 7740-7741.

The preparation of DO2S derivatives containing somatostatin analogs labeled with radiometals is shown in FIG. 3a. Direct conjugation of the DO2S derivative to the N-terminus of the selectively protected somatostatin analog octreotide is performed in the presence of activating reagents, NHS(N-hydroxysuccinimide) and DCCI (N,N-dicyclohexylcarbodiimide). This highly selective reaction does not require protection of carboxyl groups of the 1,4,7,10-tetraazacyclododecane. The partially protected octapeptides used in the coupling reactions can be synthesized in solid phase. Conjugates of the DO2S derivative and octapeptide are treated with the trifluoroacetic acid (TFA) to remove N-Boc (t-butoxycarbonyl) protecting groups from lysine to give DO2S-octreotide derivatives. This method allows for the preparation of DO2S-somatostatin analogues containing natural and non-natural amino acids with different side chains. See R. Albert, P. Smith-Jones, B. Stolz, C. Simeon, H. Knecht, C. Bruns, J. Pless, Bioorganic & Medicinal Chemistry Letters 1998, 8, 1207-1210.

Figure 3B:
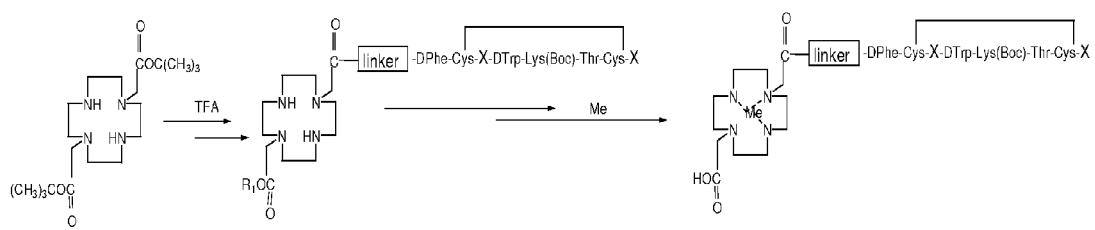
FIG. 3b illustrates the preparation of the DO2S derivative-1 containing somatostatin analogs labeled with radiometals.

FIG. 3b. illustrates the scenario where it is desirable to modulate lipophilicity of the DO2S-somatostatin analogues, different linkers can be introduced between the DO2S ring and octapeptide derivative eg. N-polyethylene glycol linkers (15-amino-4,7,10,13-tetraoxapentadecanoic acid PEG$_4$, 8-amino-3,6-dioxaoctanoic acid PEG$_2$); amino sugars (N-acetylglucosamine, N-acetylgalactosamine and their derivatives), natural and modified amino acids (Table 2). All DO2S-linker-somatostatin analogues can be synthesized by Fmoc-solid phase synthesis on H-Thr(tBu)-ol-(2-chlorotrityl)-resin. The N-terminus of the linker or the octapeptide is activated using the peptide coupling reagent, HATU (2-(1H-7-azabenzotriazol-1-yl)-1,1,3,3-tetramethyl uronium hexafluorophosphate) and then conjugated to the DO2S. The conjugates DO2S-linker-octapeptide are cleaved from the resin using TFA. In order to increase the somatostatin receptor affinity, different amino acids are incorporated in the octapeptide octreotide sequence in positions 3 and 8, and are used in the synthesis of DO2S-linker-somatostatin conjugates.

Figure 4:
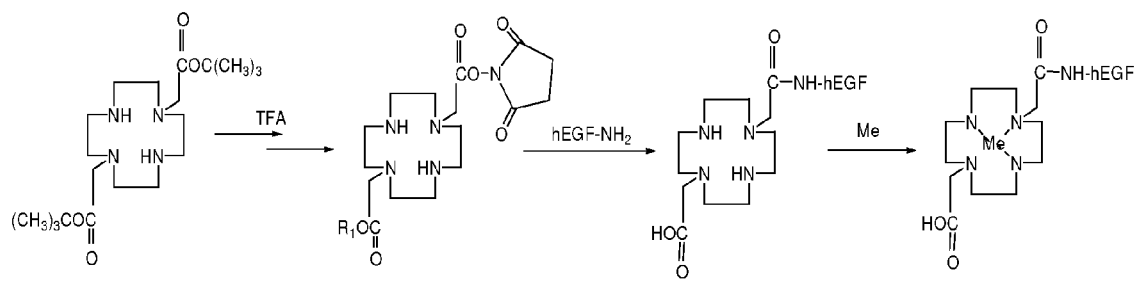
FIG. 4 illustrates the preparation of DO2S-EGF conjugates with radiometals.

Preparation of DO2S-EGF conjugates with radiometals is shown in FIG. 4. DO2S-EGF-radiometals conjugates are synthesized by a three step procedure using the N-hydroxysuccinimide ester of DO2S as a substrate. The deprotection reaction of the DO2S carboxyl group and complexation reaction of the radioisotope to the tetraaza-compound give the DO2S-EGF conjugates. See I. Velikyan et al., Journal of the Nuclear Medicine, 2005, 46 (11), 1881-1888.

FIG. 5 illustrates the preparation of the dual isotope labeled of DO2S derivatives; DO2S derivatives conjugated to aliphatic and aromatic amines, amino acids, polyamines. 5a: The α-amino and carboxylic groups of amino acids are protected with carbobenzyl (Cbz) and benzyl (Bn) groups, respectively 1. The primary amino group of the amino acid is selectively deprotected in the presence of TFA (trifluoroacetic acid), 2. Reaction of the amino acid with the bromoacetyl bromide in the presence of the DIEA (N,N-diisopropylethylamine) leads to the intermediate ester 3 which is coupled to DO2S. Protecting groups of the DO2S derivatives are removed by catalytic hydrogenation to give DO2S-modified amino acids 4. This method is used to incorporate DO2S in the exo- and endo-position of the peptide. 5b. The reaction of the amino acid (or amino containing compound) with DO2S proceeds in the presence of the peptide coupling reagents, HBTU (O-Benzotriazole-N,N,N',N'-tetramethyluronium-hexafluorophosphate)/HOBT (N-hydroxybenzotriazole) and DIEA. This method is used to prepare DO2S conjugates carrying two different labels (e.g. $^{99m}$Tc and $^{18}$F).

FIG. 6 illustrates the oxathiaphospholane approach applied for the synthesis of DO2S-phosphate, phosphorothioate, phosphoroamides, and phosphorothioamides modified with lipophylic ligand. The oxathiaphospholane approach is applied for the modification of DO2S derivatives using (thio) phosphate or phosphoro(thio)amides for conjugation to lipophilic ligands. The reaction of DO2S derivative with the 2-thiono-1,3,2-oxathiaphospholane ester proceed in the presence of Et$_3$N or DBU with release of the episulfide as a side product. This method allows for the preparation of DO2S-derivatives linked to the synthetic liposomes used as delivery vehicles for the chelating ligand. See G. W. Bailey, J. M. Corbett, R. V. W. Dimlich, J. R. Michael and N. J., Zaluzec; *Proceedings of the fifty-fourth Annual Meeting, Microscopy Society of America.* San Francisco Press, San Francisco, Calif., 1996, pp. 898-899.

Figure 7:
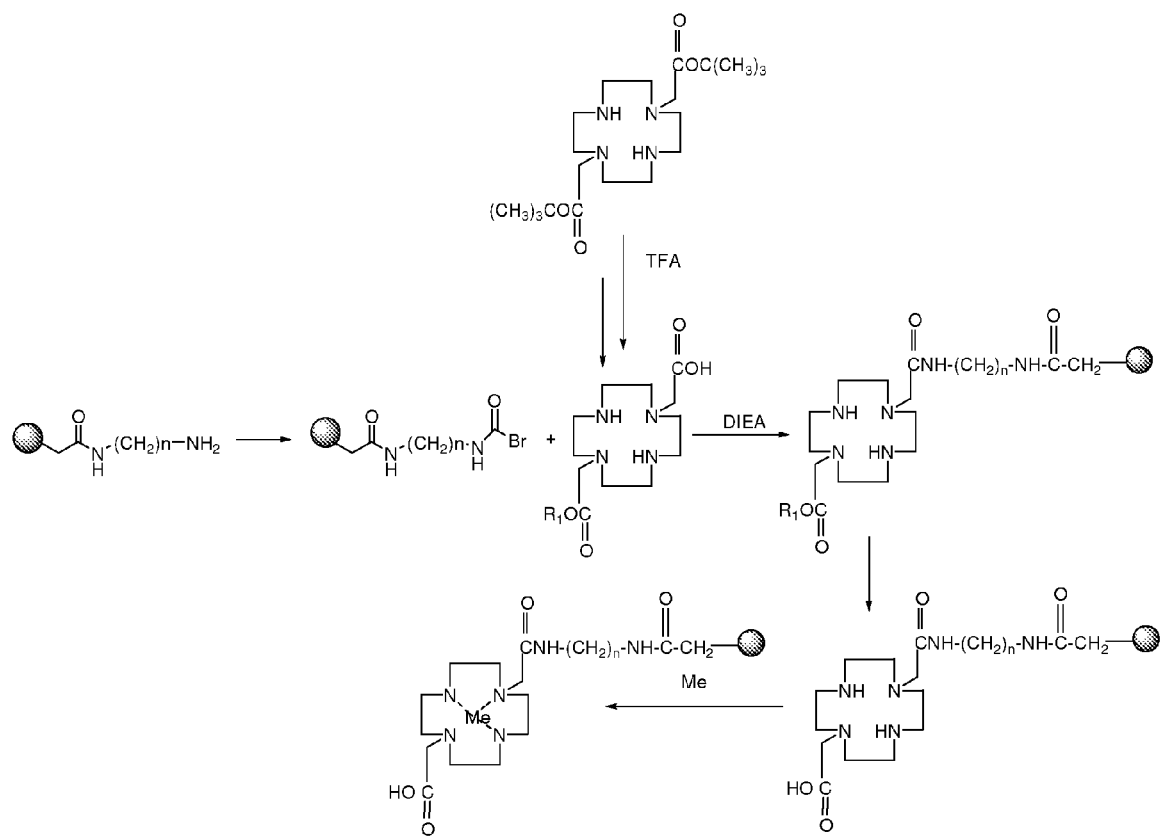
FIG. 7 illustrates the preparation of DO2S conjugates with gold nanoparticles and nanotubes.

FIG. 7 provides a schematic pathway for the preparation of DO2S conjugates with gold nanoparticles and carbon nanotubes.

FIG. 8 illustrates the modification of DO2S derivatives at the $N_4$ and/or $N_{10}$ position. The 2-bromo-N-modified acetamides alkylate the $N_4$ and/or $N_{10}$ aza-groups of the DO2A bis(t-butyl) ester. Deprotection of the carboxyl groups of DO2S derivatives proceed in the presence of trifluoroacetic acid. The carboxymethyl groups of $N_4$, $N_{10}$-disubstituted tetraaza compounds can be functionalized with other ligands using previously described methods.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A composition comprising a DO2S derivative having a structure:

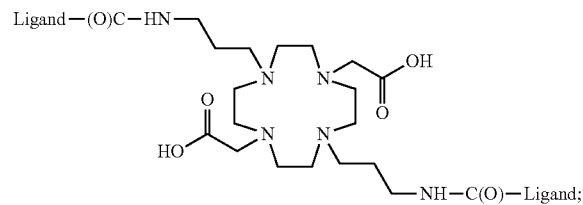

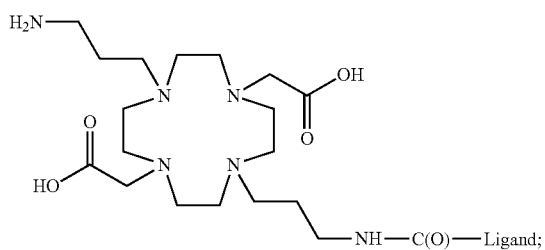

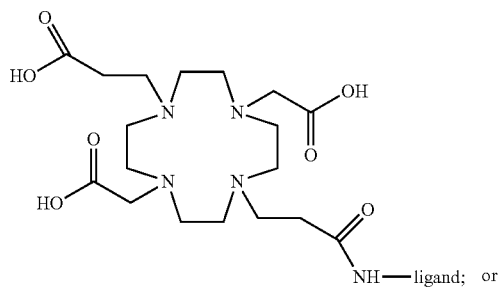

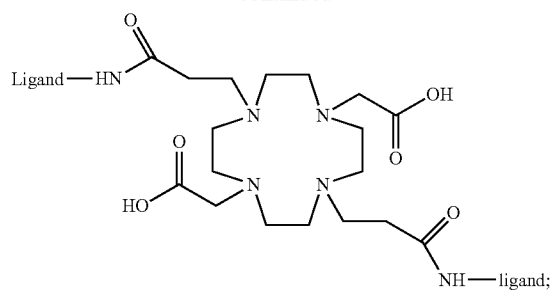

and wherein the composition is for diagnosing or treating cancer, wherein the ligand is a carbohydrate.

2. The composition of claim 1, further comprising a metal or a radionuclide chelated to the DO2S derivative.

3. The composition of claim 2, wherein the radionuclide is $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y $^{86}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi, or $^{225}$Ac.

4. A kit for the treatment or diagnosis of cancer in a subject comprising the composition of claim 1.

5. The kit of claim 4, further comprising a trans chelator selected from glucoheptonate, gluconate, glucarate, citrate, tartarate, DOTA, diethylenetriaminepentaacetic acid, or ethylenediaminetetraacetic acid.

6. The kit of claim 5, further comprising a reducing agent selected from tin (II) chloride or triphenylphosphine.

7. A composition comprising a DO2S derivative having a structure:

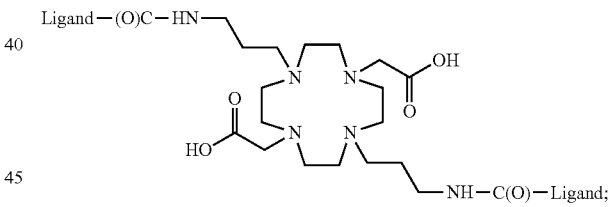

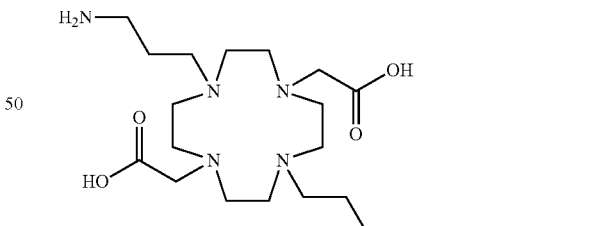

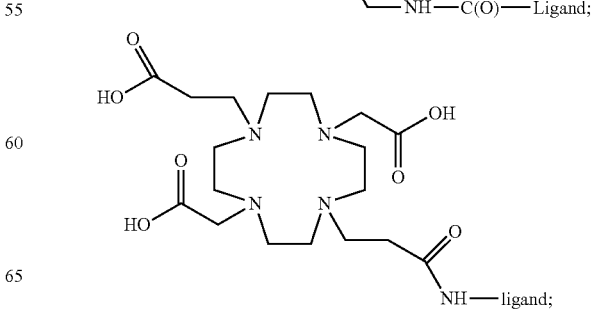

-continued

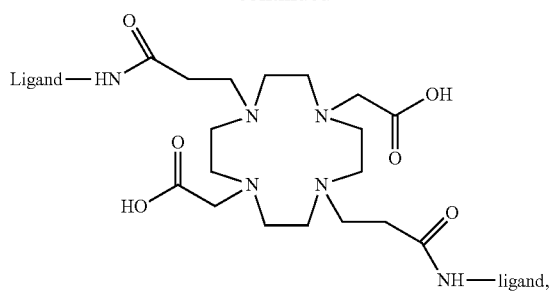

and wherein the composition is for treating cancer, wherein the ligand is a carbohydrate.

8. The composition of claim 7, wherein the DO2S derivative has a structure:

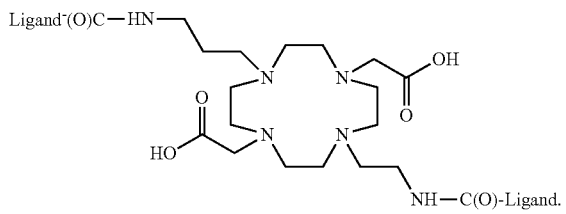

9. The composition of claim 7, wherein the DO2S derivative has a structure:

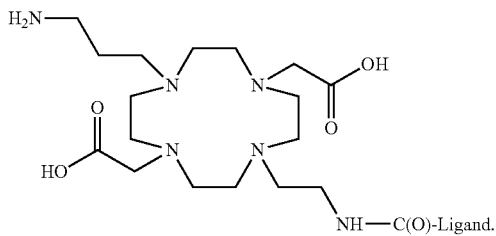

10. The composition of claim 7, wherein the DO2S derivative has a structure:

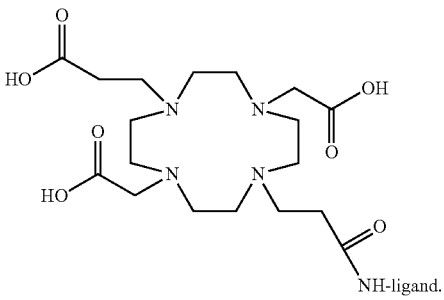

11. The composition of claim 7, wherein the DO2S derivative has a structure:

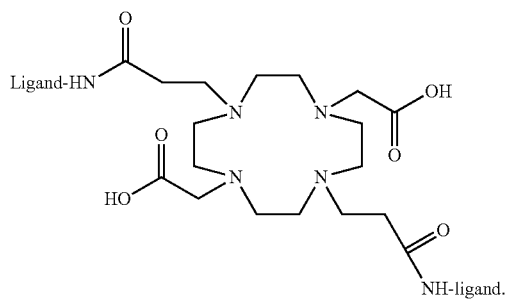

12. The composition of claim 7, further comprising a radionuclide chelated to the DO2S derivative.

13. The composition of claim 12, wherein said radionuclide is selected from the group consisting of $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{86}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi, and $^{225}$Ac.

14. A kit for the treatment or diagnosis of cancer in a subject comprising the composition of claim 7.

15. The kit of claim 14, further comprising at least one trans-chelator selected from glucoheptonate, gluconate, glucarate, citrate, tartarate, DOTA, diethylenetriaminepentaacetic acid, or ethylenediaminetetraacetic acid.

16. The kit of claim 15, further comprising a reducing agent selected from tin (II) chloride or triphenylphosphine.

* * * * *